(12) United States Patent
Anand et al.

(10) Patent No.: US 11,712,693 B2
(45) Date of Patent: Aug. 1, 2023

(54) INTEGRATED SELECTIVE CAPTURE, SEQUESTRATION, FLUIDIC ISOLATION, ELECTRICAL LYSIS AND ANALYSIS OF SINGLE CELLS

(71) Applicant: Iowa State University Research Foundation, Inc., Ames, IA (US)

(72) Inventors: Robbyn K. Anand, Ames, IA (US); Min Li, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 798 days.

(21) Appl. No.: 16/594,848

(22) Filed: Oct. 7, 2019

(65) Prior Publication Data

US 2020/0114352 A1    Apr. 16, 2020

Related U.S. Application Data

(60) Provisional application No. 62/741,662, filed on Oct. 5, 2018.

(51) Int. Cl.
  *B01L 3/00* (2006.01)
  *B03C 5/00* (2006.01)
  *C12N 13/00* (2006.01)

(52) U.S. Cl.
  CPC ........ *B01L 3/502715* (2013.01); *B03C 5/005* (2013.01); *C12N 13/00* (2013.01); *B01L 2200/0647* (2013.01); *B01L 2300/023* (2013.01); *B01L 2300/0645* (2013.01); *B01L 2300/12* (2013.01)

(58) Field of Classification Search
  CPC ....... B01L 3/502715; B01L 2300/0645; B03C 5/005; C12N 13/00
  See application file for complete search history.

(56) References Cited

U.S. PATENT DOCUMENTS

| | | | |
|---|---|---|---|
| 2016/0199853 A1 | 7/2016 | Harwood et al. | |
| 2018/0111124 A1* | 4/2018 | Anand | B01L 3/502761 |

OTHER PUBLICATIONS

Adams et al., "Highly Efficient Circulating Tumor Cell Isolation from Whole Blood and Label-Free Enumeration Using Polymer-Based Microfluidics with an Integrated Conductivity Sensor", JACS, vol. 130, No. 27, pp. 8633-8641, Mar. 3, 2008.

(Continued)

*Primary Examiner* — Brian J. Sines
(74) *Attorney, Agent, or Firm* — McKee, Voorhees & Sease, PLC

(57) ABSTRACT

A microfluidic device comprising one or more fluidic microchannels and one or more arrays of cell assay units is disclosed. Each cell assay unit in turn comprises at one bipolar electrode, micropocket, reaction chamber, and leak channel. In some embodiments, the cell assay unit further comprises two or more split BPEs inside the reaction chamber. The disclosed microfluidic device can be used to separate cells, especially rare cells, from its biological matrix and then analyze the isolated cell inside the reaction chamber. The disclosed device can isolate and analyze cells in a high-throughput fashion and without any modification or labelling to the cells. Cells isolated using the disclosed devices does not lose their vitality.

19 Claims, 13 Drawing Sheets

(56) References Cited

OTHER PUBLICATIONS

Agasti et al., "Photocleavable DNA Barcode-Antibody Conjugates Allow Sensitive and Multiplexed Protein Analysis in Single Cells", JACS, vol. 134, pp. 18499-18502, Oct. 23, 2012.

Ahmed et al., "Isolation, Detection, and Antigen-Based Profiling of Circulating Tumor Cells Using a Size-Dictated Immunocapture Chip", Angew. Chem., vol. 129, pp. 10821-10825, 2017.

Anand et al., "Negative Dielectrophoretic Capture and Repulsion of Single Cells at a Bipolar Electrode: The Impact of Faradaic Ion Enrichment and Depletion", JACS, vol. 137, pp. 776-783, Jan. 6, 2015.

Antfolk et al., "Label-free single-cell separation and imaging of cancer cells using an integrated microfluidic system", Scientific Reports, 12 pages, published Apr. 20, 2017.

Ben et al., "A Method for Detecting Circulating Tumor Cells Based on the Measurement of Single-Cell Metabolism in Droplet-Based Microfluidics", Angew. Chem. Int. Ed., vol. 55, pp. 8581-8584, 2016.

Chow et al., "A Large-Scale, Wireless Electrochemical Bipolar Electrode Microarray", JACS, vol. 131, pp. 8364-8365, Apr. 3, 2009.

Chow et al., "A Sensing Platform Based on Electrodissolution of a Ag Bipolar Elecliode", JACS, vol. 132, pp. 9228-9229, Apr. 30, 2010.

Cohen et al., "Self-Digitization of Sample Volumes", Anal. Chem., vol. 82, pp. 5707-5717, Jul. 1, 2010.

Comi et al., "Categorizing Cells on the Basis of their Chemical Profiles: Progress in Single-Cell Mass Spectrometry", JACS, vol. 139, pp. 3920-3929, Jan. 30, 2017.

Das et al., "DNA Clutch Probes for Circulating Tumor DNA Analysis", JACS, vol. 138, pp. 11009-11016, Aug. 11, 2016.

Gansen et al., "Digital LAMP in a sample self-digitization (SD) chip", Lab Chip, vol. 12, pp. 2247-2254, Feb. 6, 2012.

Green et al., "Beyond the Capture of Circulating Tumor Cells: Next-Generation Devices and Materials", Angew. Chem. Int. Ed., vol. 55, pp. 1252-1265, 2016.

Hou et al., "Polymer Nanofiber-Embedded Microchips for Detection, Isolation, and Molecular Analysis of Single Circulating Melanoma Cells", Angew. Chem. Int. Ed., vol. 52, pp. 3379-3383, 2013.

Jiang et al., "Dielectrophoretic separation with a floating-electrode array embedded in microfabricated fluidic networks", Phys. Fluids, vol. 30, 19 pages, Nov. 7, 2018.

Kasili et al., "Optical Sensor for the Detection of Caspase-9 Activity in a Single Cell", JACS, vol. 126, pp. 2799-2806, 2004.

Kim et al., "Efficient analysis of a small number of cancer cells at the single-cell level using an electroactive double-well array", Lab on a Chip, vol. 16, pp. 2440-2449, Jul. 7, 2016.

Kim et al., "Quantifying genetically inserted fluorescent protein in single iPS cells to monitor Nanog expression using electroactive microchamber arrays", Lab Chip, vol. 14, pp. 730-736, 2014.

Kobayashi et al., "Cancer Cell Analyses at the Single Cell-Level Using Electroactive Microwell Array Device", PLOS One, 10 pages, Nov. 11, 2015.

Koo et al., "Visualization and Quantification of MicroRNA in a Single Cell Using Atomic Force Microscopy", JACS, vol. 138, pp. 11664-11671, Aug. 16, 2016.

Labib et al., "Aptamer and Antisense-Mediated Two-Dimensional Isolation of Specific Cancer Cell Subpopulations", JACS, vol. 138, pp. 2476-2479, Feb. 9, 2016.

Lee et al., "Efficient Isolation and Accurate In Situ Analysis of Circulating Tumor Cells Using Detachable Beads and a High-Pore-Density Filter", Angew. Chem. Int. Ed., vol. 52, pp. 8337-8340, 2013.

Li et al., "High-Throughput Selective Capture of Single Circulating Tumor Cells by Dielectrophoresis at a Wireless Electrode Array", JACS, vol. 139, pp. 8950-8959, Jun. 13, 2017.

Park et al., "Enhanced Isolation and Release of Circulating Tumor Cells Using Nanoparticle Binding and Ligand Exchange in a Microfluidic Chip", JACS, vol. 139, pp. 2741-2749, Jan. 30, 2017.

Qiao et al., "Wirelessly powered microfluidic dielectrophoresis devices using printable RF circuits", Lab on a Chip, vol. 11, pp. 1074-1080, Jan. 4, 2011.

Qin et al., "Self-Digitization Dielectrophoretic (SD-DEP) Chip for High Efficiency Single-Cell Capture, On-Demand Compartmentalization, and Downstream Nucleic-Acid Analysis", Angew. Chem. Int. Ed., vol. 57, pp. 11378-11383, 2018.

Rakszewska et al., "Quantitative Single-Cell mRNA Analysis in Hydrogel Beads", Angew. Chem. Int. Ed., vol. 55, pp. 6698-6701, 2016.

Schneider et al., "Self-Digitization of Samples into a High-Density Microfluidic Bottom-Well Array", Analytical Chemistry, vol. 85, pp. 10417-10423, Oct. 7, 2013.

Sha et al., "Surface-Enhanced Raman Scattering Tags for Rapid and Homogeneous Detection of Circulating Tumor Cells in the Presence of Human Whole Blood", JACS, vol. 130, pp. 17214-17215, Jun. 12, 2008.

Thompson et al., "Self-Digitization Microfluidic Chip for Absolute Quantification of mRNA in Single Cells", Analytical Chemistry, vol. 86, pp. 12308-12314, Nov. 12, 2014.

Wang et al., "Three-Dimensional Nanostructured Substrates toward Efficient Capture of Circulating Tumor Cells", Angew. Chem. Int. Ed., vol. 48, pp. 8970-8973, 2009.

Wu et al., "High-Throughput Separation, Trapping, and Manipulation of Single Cells and Particles by Combined Dielectrophoresis at a Bipolar Electrode Array", Analytical Chemistry, vol. 90, pp. 11461-11469, Sep. 7, 2018.

Xue et al., "Chemical Methods for the Simultaneous Quantitation of Metabolites and Proteins from Single Cells", JACS, vol. 137, pp. 4066-4069, Mar. 19, 2015.

Zhang et al., "Hand-Held and Integrated Single-Cell Pipettes", JACS, vol. 136, pp. 10858-10861, Jul. 18, 2014.

Zhang et al., "Single-Cell Mass Spectrometry Approaches to Explore Cellular Heterogeneity", Angew. Chem. Int. Ed., vol. 57, pp. 4466-4477, 2018.

* cited by examiner

Valve-free Channel Design

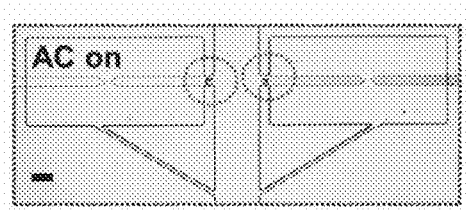
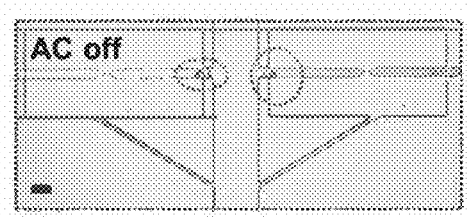
FIG. 6A                FIG. 6B
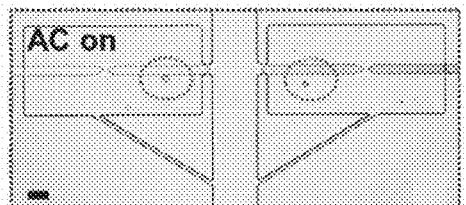
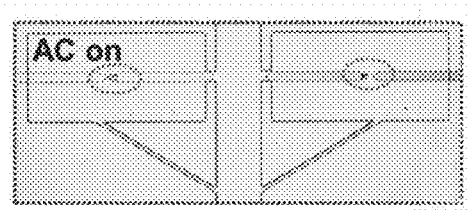
FIG. 6C                FIG. 6D
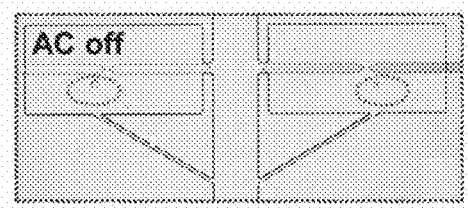
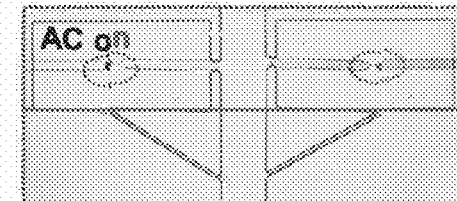
FIG. 6E                FIG. 6F
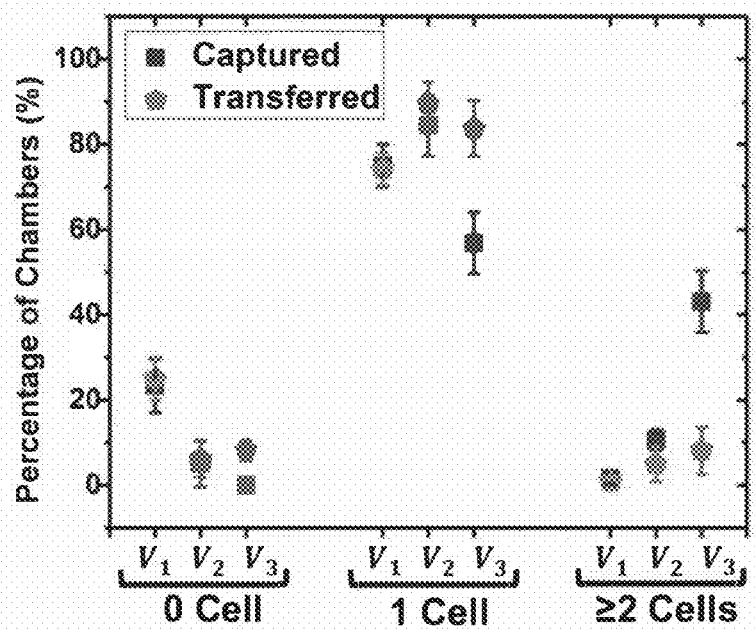
FIG. 6G

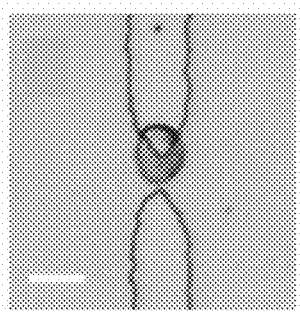
FIG. 7A
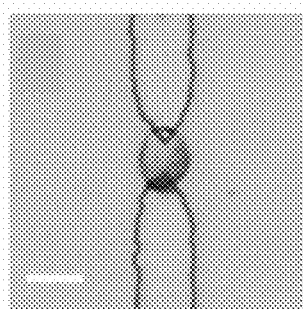
FIG. 7B
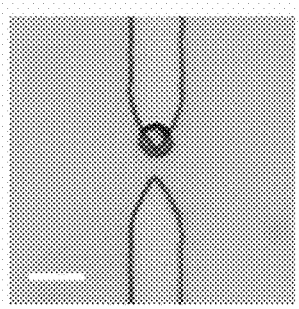
FIG. 7C
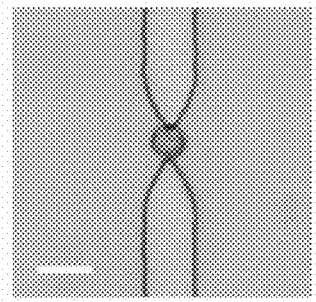
FIG. 7D
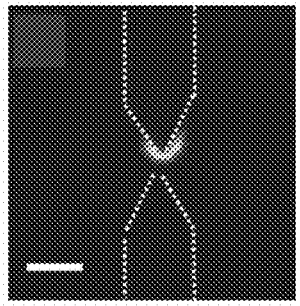
FIG. 7E
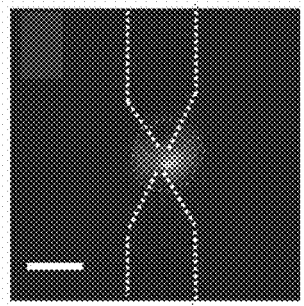
FIG. 7F
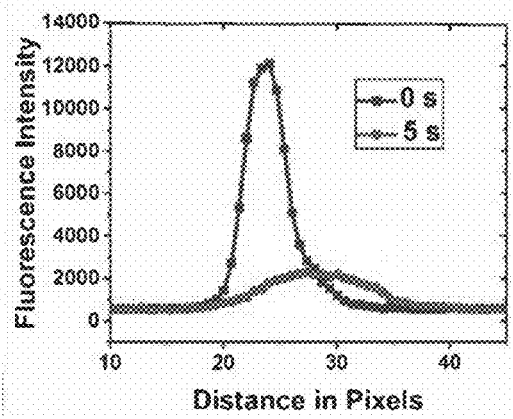
FIG. 7G
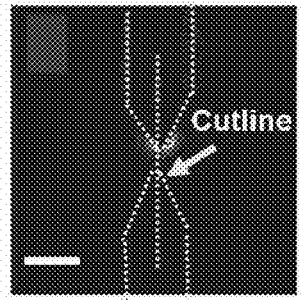
FIG. 7H
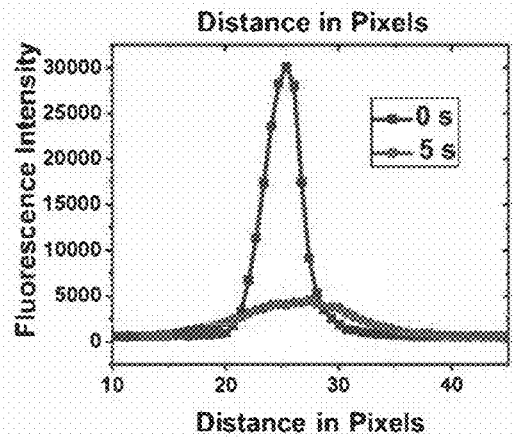
FIG. 7I
FIG. 7J

INTEGRATED SELECTIVE CAPTURE, SEQUESTRATION, FLUIDIC ISOLATION, ELECTRICAL LYSIS AND ANALYSIS OF SINGLE CELLS

CROSS-REFERENCE TO RELATED APPLICATION

This application claims priority under 35 U.S.C. § 119 to Provisional Application U.S. Ser. No. 62/741,662, filed on Oct. 5, 2018, which is herein incorporated by reference in its entirety including without limitation, the specification, claims, and abstract, as well as any figures, tables, or examples thereof.

FIELD OF THE INVENTION

The present invention relates to a microfluidic device for selective single-cell capture at an array of wireless bipolar electrodes (bipolar electrodes, BPEs), i.e., selective cell isolation, retention, necessary reagent exchange, fluidic isolation, and rapid electrical lysis for high-throughput analysis. The device is capable of not only capturing a targeted cell but also of manipulating and preparing the captured cell for high-throughput analysis simply by exchanging the solution in a single inlet reservoir and by adjusting the applied voltage at a pair of driving electrodes. The device is thus well-suited for point-of-care applications at medical facilities.

BACKGROUND OF THE INVENTION

Differentiating or separating a few cells from a matrix or mixture containing multiple cell types is a challenging and exciting task that is in high demand. For example, the need to study circulating tumor cells (CTCs) and the potential impact of isolating CTCs (either single CTC cell or microemboli of CTCs) make a compelling argument for the need for new devices and methods capable of rare cell isolation.

CTCs are cells that have detached from the primary tumor and migrated into blood vessels. A fraction of these CTCs seed metastases by extravasation into the parenchyma of foreign tissues for subsequent growth of tumors. Understanding and preventing this process is critical because metastasis leads to 90% of epithelial cancer-related deaths.

Recent years have witnessed growing efforts to study CTCs for the development of effective therapies. For instance, clinical studies have shown that an inverse correlation exists between survival and the number of CTCs. This correlation is independent of the line of therapy. Clinical studies have also shown that the reduction or elimination of CTCs after treatment prolongs survival. These findings indicate that the enumeration of CTCs is relevant for diagnosis, prognosis, and evaluation of drug resistance. Additionally, the genetic mutations exhibited in CTCs may provide guidance for the selection of therapies, thus personalizing treatment. For example, metastatic colorectal cancer patients with wild-type KRAS can benefit from anti-epidermal growth factor receptor (EFGR) monoclonal antibody (mAb) treatment, while those with mutated KRAS are not able to use this monotherapy. In this scenario, the study of CTCs including isolation and characterization is of paramount importance for the successful preparation and implementation of anticancer therapies.

Despite CTCs' promise as a clinical indicator and therapeutic target, the separation of CTCs from whole blood, which is the first inevitable step of overall analysis, is challenging. First, CTCs are extremely rare, such that there can be as few as 1 CTC per $10^9$ erythrocytes and $10^7$ leukocytes. In a standard blood sample with a volume of 7.5 mL employed, the number of CTCs detected by techniques that are currently clinically available is normally less than 10.

Second, due to the heterogeneous nature of the cell populations found in primary tumors and the changes undergone by these cells during metastatic events, the phenotypic characteristics of CTCs can vary widely. Examples include the nuclear to cytoplasmic ratios (N/C) (The average N/C ratio of CTCs in breast cancer patients is 4.0, while it is 1.43 in prostate cancer patients), deformability (CTCs with large N/C ratio are less deformable and less invasive), size (the size of CTCs reported is over a wide range from 4 µm to 30 µm, even from a single patient) and protein expression. The proteins such as cytokeratin (CK) and epithelial cell adhesion molecules (EpCAM) present on the surface of tumor cells vary tremendously depending on the patient, the type of cancer, and the stage of the tumor.

Despite these challenges, tremendous progress has been made using one or more of CTCs' unique properties to discriminate or isolate them from surrounding blood cells. For example, the use of dielectrophoresis (DEP) at a wireless bipolar electrode (BPE) array was demonstrated to be suitable for selective and high-throughput single-cell capture as disclosed in U.S. patent application Ser. No. 15/793,587, which was filed Oct. 25, 2017, is titled "HIGH-THROUGHPUT SELECTIVE CAPTURE OF BIOLOGICAL CELLS BY DIELECTROPHORESIS AT A BIPOLAR ELECTRODE ARRAY", and is herein incorporated by reference in its entirety. In the disclosed devices, BPE tips aligned to the micropockets along the fluidic microchannel could accomplish great than 80% single-cell capture while discriminating CTCs from a background of white blood cells (WBCs). Since BPEs do not require wire leads (direct electrical connection), the disclosed devices allow from 2 to 32 parallel fluidic microchannels, which greatly increased throughput while retaining capture efficiency.

However, the disclosed devices in Ser. No. 15/793,587 application are not suitable to incorporate any on-chip cell analysis because the capture efficiency of those devices is coupled with the geometry of the micropocket, and therefore, the reaction volume could not be independently tuned. Even a recent disclosed device, self-digitization dielectrophoretic (SD-DEP) chip for high efficiency single-cell capture, on-demand compartmentalization, and downstream nucleic-acid analysis, the flow-through micropockets employed are not readily amenable to a bifurcation scheme, thus significantly limiting throughput. And, the fluidic resistance of these micropockets was sufficiently low that imbalances in pressure resulted in both disruption of cell capture and intrusion of flow fluid into the micropockets.

Accordingly, it is an objective of the disclosure to provide an integrated and improved microfluidic device for both selective single-cell capture at an array of wireless electrodes (bipolar electrodes, BPEs), i.e. selective cell isolation and retention, and necessary reagent exchange, fluidic isolation, and rapid electrical lysis for high-throughput analysis of the captured cell.

It is also an objective of this disclosure to provide a method for utilizing the microfluidic devices disclosed herein for separation of a certain type of cells from all other types of cells and its subsequent on-chip analysis and characterization.

The disclosed microfluidic devices, while retaining the inherent advantages of DEP for selective and label-free isolation of cells and ease of fabrication, provide an avenue for point-of-care applications.

Other objects, advantages and features of the present invention will become apparent from the following specification taken in conjunction with the accompanying examples or drawings.

BRIEF SUMMARY OF THE INVENTION

In one aspect, the present disclosure provides a microfluidic device, the device comprises one or more fluidic microchannels that are configured to retain and move an ionically conductive solution; and one or more arrays of cell assay units, wherein each array of the cell assay units comprises two or more of the cell assay units; wherein each cell assay unit comprises a reaction chamber, leak channel, micropocket, and at least one bipolar electrode (BPE), and wherein the one or more arrays of the cell assay units are placed along the one or more fluidic microchannels.

In another aspect, the present disclosure provides a system for isolating and analyzing or characterizing a specific cell, wherein the system comprises a microfluidic device disclosed herein and an ionically conductive solution.

In another aspect, the present disclosure provides a method for isolating and analyzing or characterizing a cell from a biological matrix. The method comprises contacting a biological sample with an ionically conductive solution in a fluidic device disclosed herein and applying an AC electric field to the bipolar electrodes in the micropockets for a period of time so a targeted cell is trapped at the tip of the bipolar electrode inside the micropocket; wherein the targeted cell is subsequently transferred to a reaction chamber for analysis or characterization, and wherein the biological sample contains the targeted cell to be isolated.

Thus, the microfluidic devices disclosed herein integrates selective single-cell capture, transport and isolation with parallel lysis and analysis in one microfluidic platform. These devices are scalable for high-throughput analysis or characterization of selected cells.

The advantages for the disclosed devices include, but are not limited to, (1) it addresses a need for development of versatile devices that integrate all steps needed for single-cell analysis (selection, isolation, assays), (2) the whole manipulation process (selective single-cell capture, cell transfer, cell retention, and cell lysis) was valve-free and achieved by only exchanging the fluids, adjusting fluid flow rates, and/or changing electric field gradients and a single applied voltage, and (3) the use of wireless bipolar electrodes (BPEs) allows facile arraying, high-throughput sorting, and analysis of individual cells.

The microfluidic devices disclosed herein integrate the advantages of both the BPE and self-digitization (SD) schemes to accomplish selection, isolation, electrical lysis, and analysis in a valve-free and robust platform with a single inlet.

Although the SD scheme is used to specifically address the need for an isolated reaction volume—an oil phase sealed off the narrow constrictions leading to the reaction chambers, there are three key distinctions for the claimed devices. First, there is only one fluidic layer, which greatly simplifies fabrication. Second, cell capture is accomplished at a micropocket other than a reaction chamber (i.e., not at the bottom of a reaction well), which critically provides independent control over the reaction volume in the reaction chamber and the capture efficiency at the micropocket. Third, and most importantly, the cell assay unit structures are readily fluidically isolated by an immiscible phase (SD principle) to prevent assay crosstalk. the claimed devices are not a simple combination of the BPE and SD schemes.

In addition, a split BPE inside the reaction chamber can be incorporated to allows electric field-directed cell recapture and electrical lysis. Use of ionic liquids as a substitute for oil allows electrical lysis, which is fast, low cost, and easy to operate. These modifications are accomplished with minimal peripheral equipment—a power supply and a microscope—thus making the claimed devices for point-of-care applications possible.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A shows an exemplary position of a BPE, micropocket, reaction chamber, and leak channel within a cell assay unit. FIG. 1B and FIG. 1C shows two exemplary arrangements of several cell assay units with their respective reaction chambers, micropockets, and leak channels along a main flow microchannel.

FIG. 6A-FIG. 6F show results of the cell re-capture step using split BPEs, time lapse images of cell capture, transfer, and recapture accomplished by only turning on and off the applied voltage.

FIG. 6G shows the optimization of applied voltage for cell capture and transfer when split BPEs were employed (the scale bar is 50 µm).

FIG. 7A-FIG. 7J show the results of using split BPEs inside the reaction chamber and a higher voltage for cell lysis.

DETAILED DESCRIPTION OF THE INVENTION

Figure 1A:
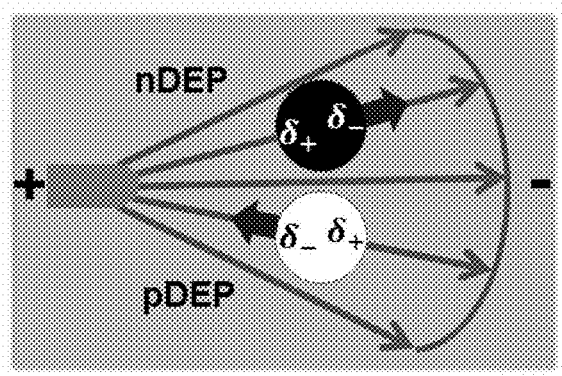
FIG. 1A shows the principles of pDEP attraction and nDEP repulsion in an external electric field.

The present disclosure relates to a microfluidic device comprising one or more arrays of cell assay units, each of which comprises a reaction chamber, micropocket, leak channel, and at least one wireless bipolar electrode (BPE), to separate one type of cells from all other types of cells. The embodiments of this invention are not limited to any particular device, which can vary and are understood by skilled artisans based on the present disclosure herein. It is further to be understood that all terminology used herein is for the purpose of describing particular embodiments only and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range (i.e. 1 to 5 includes 1, 1.5, 2, 2.75, 3, 3.80, 4, and 5).

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation. The preferred materials and methods are described herein. In describing and claiming the embodiments of the present invention, the following terminology will be used in accordance with the definitions set out below.

The term "about," as used herein, refers to variations in size, distance or any other types of measurements that can be resulted from inherent heterogeneous nature of the measured objects and imprecise nature of the measurements itself. The term "about" also encompasses variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods, and the like. The term "about" also encompasses amounts that differ due to different equilibrium conditions for a composition resulting from a particular initial mixture. Whether or not modified by the term "about", the claims include equivalents to the quantities.

The present disclosure provides a microfluidic device comprising one or more arrays of wireless bipolar electrodes. A bipolar electrode (BPE) is a conductor that, when exposed to an external electrical field, can facilitate oxidation and reduction reactions simultaneously at its opposite ends. For example, a BPE can comprise a strip of metal embedded in a microfluidic channel filled with an aqueous electrolyte.

Manipulation of Cells by Dielectrophoresis (DEP)

DEP is a field-induced force (FDEP) exerted on a particle due to the interaction of the particle's dipole moment (P) with the spatial gradient of the electric field ($\nabla E$). As shown in FIG. 1A, when particles are placed in an external electric field (E), the field induces partial charges ($\delta^+$ and $\delta^-$) at the particle-medium interfaces via free charge and/or polarization charge. The non-uniformity of the electric field ($\nabla E$) results in each half of the dipole experiencing a different magnitude of electrostatic force, thereby leading to movement of the particle. In a linearly polarized sinusoidal field, the time-averaged DEP force (FDEP) of a homogeneous spherical particle is given by:

$$\vec{F}_{DEP} = 2\pi r^3 \varepsilon_m Re[K(\omega)] \vec{\nabla} |\vec{E}|^2 \qquad (1)$$

Where $Re[K(\omega)]$ is the real part of the Clausius-Mossotti factor, $$K(\omega) = \frac{\varepsilon_p^* - \varepsilon_m^*}{\varepsilon_p^* + 2\varepsilon_m^*} \qquad (2)$$

$\varepsilon^*_p$ and $\varepsilon^*_m$ are the frequency-dependent complex permittivities of the particle and medium, respectively. $Re[K(\omega)]$, which falls within a range of $-0.5$ to $+1.0$, indicates the direction and relative strength of FDEP experienced by the particle. When $Re[K(\omega)]$ is negative, the case when the particle is relatively less polarizable than the medium, the net FDEP directs particles toward lower electric field (negative DEP, or nDEP). Accordingly, a positive value of $Re[K(\omega)]$ indicates particle displacement toward higher electric field (positive DEP or pDEP). Due to the high sensitivity of DEP responses to particle composition, DEP has been widely employed in applications including particle separation, biopatterning, and transport of selected particles to specific locations where additional processes can occur.

Bipolar Electrode (BPE) in an AC Electrical Field

Figure 1B:
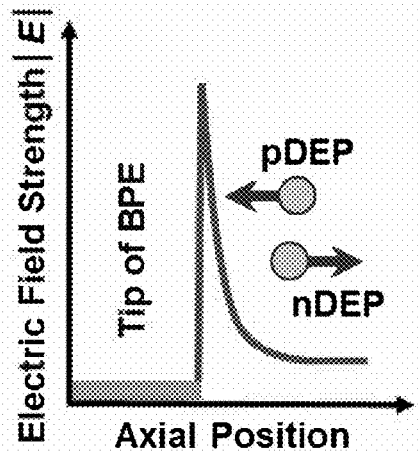
FIG. 1B and FIG. 1C show pDEP attraction and nDEP repulsion in an external electric field near a BPE tip.
Figure 1C:
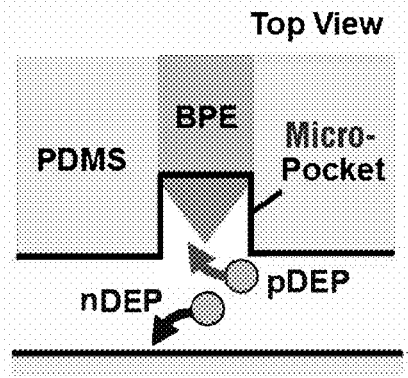

Bipolar electrode (BPE) refers to a conductor that lacks ohmic contact to an external power supply (i.e., 'wireless') and that, in the presence of a DC electric field applied by external driving electrodes can facilitate coupled faradaic reactions at its ends. The current path between the two external driving electrodes is either via ionic conduction in solution ($R_s$) or charge transfer ($R_{ct}$) at the BPE. It has been demonstrated the possibility of another current path via capacitive charging of the electrical double layer (EDL) at opposing ends of each BPE under an AC electric field. This application of BPEs in an AC electric field made it possible to develop DEP devices that capture cells at wireless electrode arrays defining up to 1,400 capture sites. For example, alignment of the BPE tips to cell-sized micropockets allows single-cell selection and isolation as shown in FIG. 1B and FIG. 1C.

Cell Assay Units

The microfluidic devices disclosed herein comprise arrays of cell assay units along each fluidic microchannel. Each cell assay unit in turn comprises a reaction chamber, a micropocket, a leak channel, and at least one wireless bipolar electrode (BPE). Within each cell assay unit, its micropocket is fluidically connected to both the reaction chamber and the fluidic microchannel and its leak channel fluidically connects the reaction chamber and the fluidic microchannel. An array of the cell assay units is positioned along a wall of a fluidic microchannel. The BPEs in each array of the cell assay units are electronically connected, but each reaction chamber, micropocket, and leak channel are separated from each other.

Figure 2C:
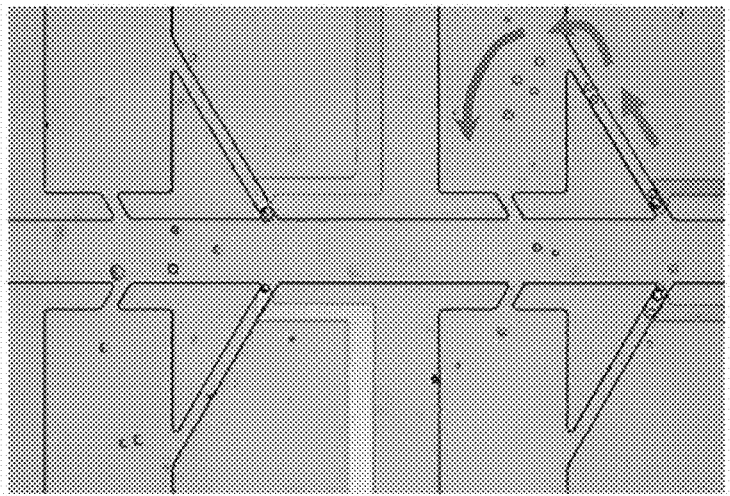
FIG. 2A-FIG. 2C show the illustrations of a cell assay unit along a fluidic microchannel.
Figure 2B:
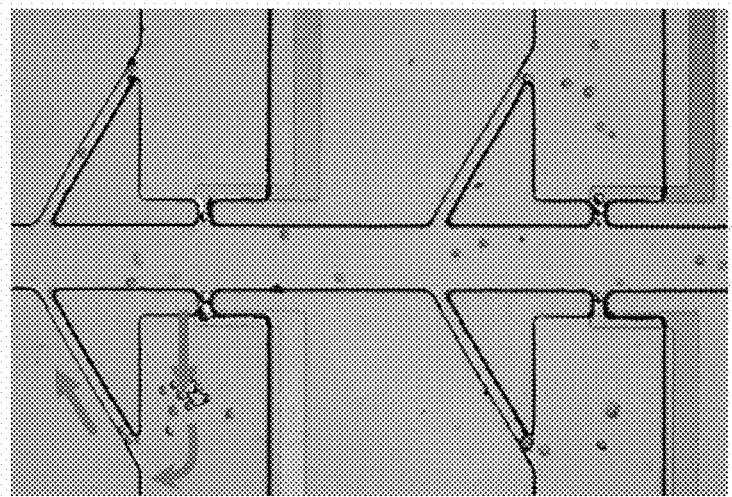
Figure 2A:
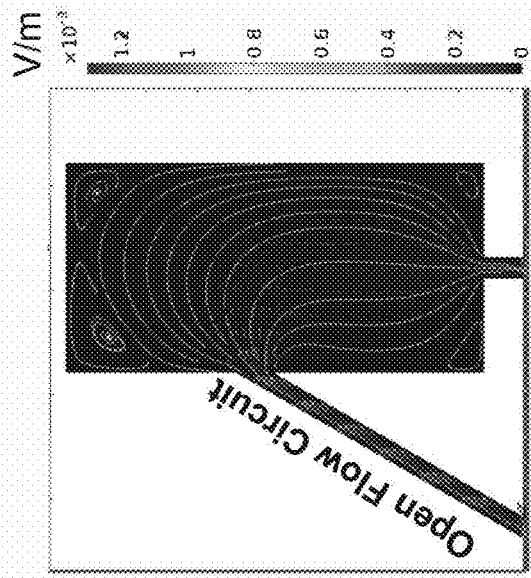

FIG. 2A-FIG. 2C show exemplary diagram of a cell assay unit and its components' positional relationship with a fluidic microchannel. FIG. 2A-FIG. 2C show the illustrations of a cell assay unit along a fluidic microchannel. FIG. 2A shows an exemplary position of a BPE, micropocket, reaction chamber, and leak channel within a cell assay unit. FIG. 1B and FIG. 1C shows two exemplary arrangements of several cell assay units with their respective reaction chambers, micropockets, and leak channels along a main flow microchannel.

Figure 3A:
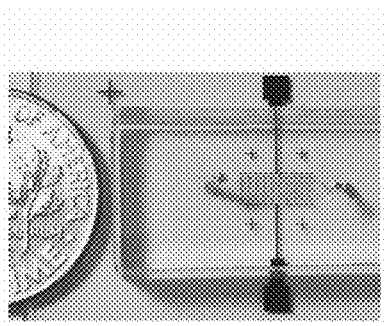
FIG. 3A illustrates the scale of the device.
Figure 3B:
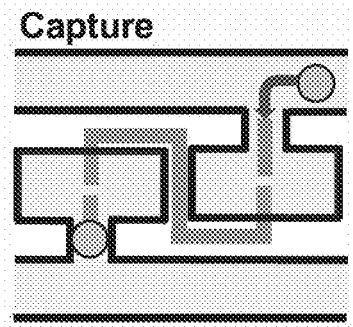
FIG. 3B-FIG. 3H illustrate the steps of operation of the exemplary microfluidic device.
Figure 3C:
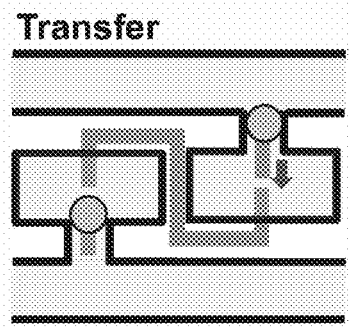
Figure 3D:
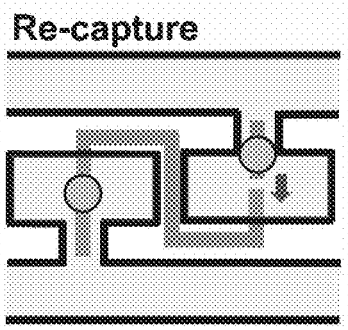
Figure 3E:
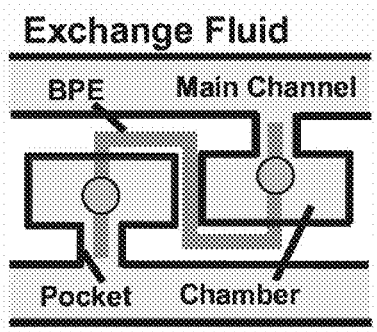
Figure 3F:
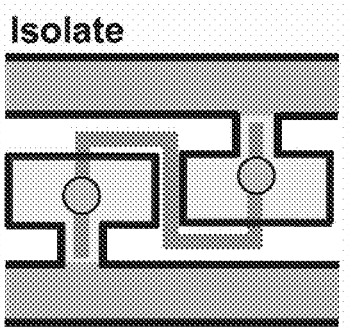
Figure 3G:
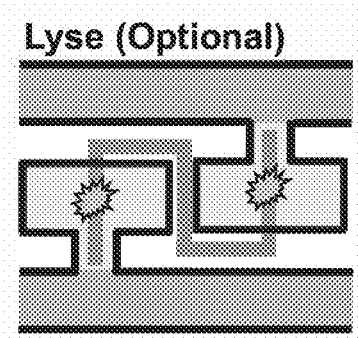
Figure 3H:
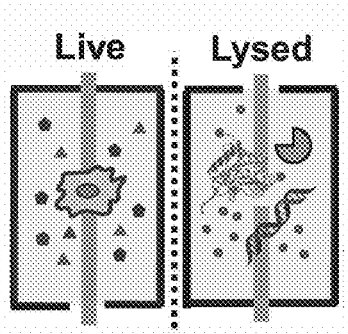

The microfluidic devices disclosed herein are capable of analysis or characterization of the captured cells. FIG. 3A illustrates the scale of the device. FIG. 3B-FIG. 3H illustrate the steps of operation of the exemplary microfluidic device: (i) When an AC electric field is applied, cells of interest are selectively separated and individually isolated near the tips of BPEs, which are located at one opening of the micropocket as shown in FIG. 3B; (ii) By turning the AC field 'off' and then 'on' again, the captured single-cells are further directed forward and retained at the center of the reaction chambers between adjacent BPE tips as shown in FIG. 3C and FIG. 3D; At this juncture, the fluid can be exchanged if warranted by the assay as shown in FIG. 3E; (iii) The microchannel is then filled with a hydrophobic ionic liquid to fluidically isolate the chambers as shown in FIG. 3F; and (iv) The AC field strength is then increased to lyse captured cells for assay of intracellular contents as shown in FIG. 3G and FIG. 3H.

In some embodiments, the distance between adjacent cell assay units is from about 10 μm to about 500 μm, from about 25 μm to about 500 μm, from about 0.05 mm to about 0.5 mm, from about 0.05 mm to about 0.1 mm, from about 0.05 mm to about 0.15 mm, from about 0.05 mm to about 0.2 mm, from about 0.05 mm to about 0.25 mm, from about 0.05 to about 0.3 mm, from about 0.05 mm to about 0.35 mm, from about 0.05 mm to about 0.4 mm, from about 0.05 mm to about 0.5 mm, from about 0.1 to about 0.15 mm, from about 0.1 mm to about 0.2 mm, from about 0.1 mm to about 0.25 mm, from about 0.1 to about 0.3 mm, from about 0.1 mm to about 0.35 mm, from about 0.1 mm to about 0.4 mm, from about 0.1 mm to about 0.5 mm, about 0.05 mm, about 0.1 mm, about 0.15 mm, about 0.2 mm, about 0.25 mm, about 0.3 mm, about 0.35 mm, about 0.4 mm, about 0.5 mm, or any value there between.

In one aspect, the present disclosure provides a microfluidic device, the device comprises one or more fluidic microchannels that are configured to retain and move an ionically conductive solution; and one or more arrays of cell assay units, wherein each array of the cell assay units comprises two or more of the cell assay units; wherein each cell assay unit comprises a reaction chamber, leak channel, micropocket, and at least one bipolar electrode (BPE), and wherein the one or more arrays of the cell assay units are placed along the one or more fluidic microchannels.

Within each cell assay unit, its micropocket connects the microfluidic channel and the reaction chamber and hosts the at least one BPE; and its leak channel also connects the reaction chamber and the fluidic microchannel.

Microchannel, Fluidic Microchannel, or Main Microchannel

As used herein, a microchannel, fluidic microchannel, and main microchannel are used interchangeably and each of them is referred to as a passageway with a cross section of from a few micrometers (several $10^{-6}$ meters) to about a few hundred micrometers (hundreds $10^{-6}$ meters) and with a length of from a few hundred micrometers (hundreds $10^{-6}$ meters) to about a few millimeters (several or tens $10^{-3}$ meters). The cross section of a microchannel in principle can have any two-dimensional shape, such as square, rectangular, circle, or a combination thereof. A microchannel may be straight or curved. In some embodiments, a microchannel may be encircled by a wall or several walls or by a complete circular wall, except two openings at both ends. In some embodiments, a microchannel does not have its top wall.

In some embodiments, the wall(s) or some parts of the wall of a microchannel is a part of the wireless bipolar electrodes or other conductive or nonconductive parts of the microfluidic device. In some embodiments, the wall(s) or some parts of the wall of a microchannel comprises polymeric material, conductive, non-conductive, semi-conductive material, or a combination thereof.

In some other embodiments, the microfluidic devices disclosed herein have 1, 2, 4, 8, 16, 32, 64, or much more microchannels. A number of microchannels can be grouped together and then connected fluidly with another group(s) of microchannels. Two or more microchannels are grouped together by fluidly connecting their ends. Within each group of microchannels, any two microchannels can be parallel to each other, on top of each other, or in another arrangement.

In some embodiments, one or more microchannels are the same. In some other embodiments, one microchannel can be different from other microchannels in the same microfluidic devices.

In some embodiments, a few microchannels can merge into a bigger channel or reservoir for design or throughput purposes to form a merged microchannel or reservoir. As the result of merging, a merged microchannel or reservoir has the combined size or footprint of the microchannels that are merged. In this situation, the walls or barriers between merged microchannels are dismantled or removed.

As used herein, the width of a microchannel is referred to as the horizontal distance of the two points that are on the opposite edges of the cross section along the intended fluidic flow and are furthest away from each other. As used herein, the height of a microchannel is referred to as the vertical distance of the points that one of the opposite edges of the cross section along the intended fluidic flow and are furthest away from each other. As used herein, the length of a microchannel is the distance between the two ends along the intended fluid flow. The length of a microchannel is usually the length of its longest dimension. The two shorter dimensions usually defines the cross section described above.

In some embodiments, within each microchannel of the disclosed microfluidic device, there are one or more arrays of cell assay units along the wall(s) of the microchannels. The arrays of cell assay units can be on the bottom/floor wall(s), side wall(s), or top walls of the microchannel.

Bipolar Electrode (BPE) or Array of Bipolar Electrodes

As used herein, a wireless bipolar electrode is referred to as a piece of conductive or semi-conductive material comprising two ends as one skilled in the art would understand. A wireless bipolar electrode as used herein has dimensions within from about a few micrometers to about a few millimeters. A wireless bipolar electrode used in this disclosure does not require a lead or ohmic connection to a power source.

As used herein, an array of wireless bipolar electrodes (BPEs) refers to a group of at least two or more wireless bipolar electrodes. And within the group any one of the wireless bipolar electrodes is connected via an ionically conductive medium with at least one other wireless bipolar electrode. Two or more arrays of wireless BPEs can be connected with each other electronically or conductively through the ends of each array.

In some embodiments of the fluidic devices disclosed herein, each BPE of the arrayed BPEs is inside its respective the cell assay unit. Specifically, each cell assay unit comprises at least one BPE in its micropocket and can further comprises two or more split BPEs inside its reaction chamber.

As used herein, split BPEs are two or more separated BPEs that originated from a single BPE.

In some embodiments, a wireless BPE is parallel to the other wireless BPEs in the same array. In some embodiments, a wireless BPE is aligned with another wireless BPE in a different array of wireless BPEs within the same microchannel, merged microchannel, or reservoir formed by the merged microchannels. In some other embodiments, an array of wireless BPEs are staggered with another array of wireless BPEs within the same microchannel, merged microchannel, or reservoir formed by the merged microchannels.

Micropocket

As used herein, a micropocket or microchamber is referred to as a micro scale space at least partially enclosed by the materials of other components of the microfluidic devices or by its own wall(s). As used herein, the term "microchamber" and "micropocket" are used interchangeably. In some embodiments, a micropocket hosts one end of a wireless BPE and has an opening to a microchannel, merged microchannel, or reservoir formed by the merged microchannels. In some embodiments, a microchamber has a dimension of from about a few micrometers to about a few hundred micrometers of its width, height, and depth.

As used herein, the width of a micropocket is referred to the horizontal distance of the two points that are on the opposite edges of the cross section along the wall of the microchannel and are furthest away from each other. As used herein, the height or tallness of a micropocket is referred to the vertical distance of the points that are on the opposite edges of the cross section on the wall of the microchannel and are furthest away from each other. As used herein, the length of a micropocket is the shortest distance from the edge of the fluid flow to the edge of the reaction chamber that the micropocket connects to.

A micropocket can have any shape as one skilled in the art can understand. The cross section of a micropocket can have any two-dimensional shape. In some embodiments, the cross section of a micropocket can be regular or irregular a square, rectangle, circle, or a combination thereof. In some embodiments, the cross section of a micropocket is a regular rectangle.

In some embodiments, the cross section of a micropocket is uniform along its entire length. In some other embodiments, the cross section of a micropocket is not uniform along its entire length.

In some embodiments, all micropockets are the same. In some other embodiments, one or some of the micropockets in a disclosed microfluidic device can be different from other microchambers in the same microfluidic device.

In some embodiments, a micropocket connects with a reaction chamber at an angle of from about 15° to 90°. In some other embodiments, a micropocket connects with a microchannel at an angle of from about 15° to 90°.

In some embodiments, a microchamber is inside a wall of the microchannels, merged microchannels, or reservoir formed by the merged microchannels.

In some embodiments, a microchamber does not have one or two of its top wall(s), floor wall(s), or side walls.

In some embodiments, the power source is not in direct contact with the wireless bipolar electrodes.

In some other embodiments, the one or more fluidic microchannels have a width of from about 10 μm to about 200 μm, from about 5 μm to about 200 μm, from about 1 μm to about 200 μm, from about 10 μm to about 20 μm, from about 10 μm to about 30 μm, from about 10 μm to about 40 μm, from about 10 μm to about 50 μm, from about 10 μm to about 60 μm, from about 10 μm to about 70 μm, from about 10 μm to about 80 μm, from about 10 μm to about 90 μm, from about 10 μm to about 100 μm, from about 10 μm to about 120 μm, from about 10 μm to about 140 μm, from about 10 μm to about 160 μm, from about 10 μm to about 180 μm, or from about 1, 2, 5, 10, 15, or 20 μm to any value between 25 μm and 200 μm. In some other embodiments, the width of the one or more fluidic microchannels is about 10 μm, about 20 μm, about 30 μm, about 40 μm, about 50 μm, about 60 μm, about 70 μm, about 80 μm, about 90 μm, about 100 μm, about 110 μm, about 120 μm, about 130 μm, about 140 μm, about 150 μm, about 160 μm, about 170 μm, about 180 μm, about 190 μm, about 200 μm, or about any value there between.

In some other embodiments, the one or more fluidic microchannels have a height of from about 10 μm to about 100 μm, from about 5 μm to about 100 μm, from about 10 μm to about 15 μm, from about 10 μm to about 20 μm, from about 10 μm to about 25 μm, from about 10 μm to about 30 μm, from about 10 μm to about 35 μm, from about 10 μm to about 40 μm, from about 10 μm to about 45 μm, from about 10 μm to about 50 μm, from about 10 μm to about 55 μm, from about 10 μm to about 60 μm, from about 10 μm to about 70 μm, from about 10 μm to about 80 μm, from about 10 μm to about 90 μm, from about 15 μm to about 20 μm, from about 15 μm to about 25 μm, from about 15 μm to about 30 μm, from about 15 μm to about 35 μm, from about 15 μm to about 40 μm, from about 15 μm to about 45 μm, from about 15 μm to about 50 μm, from about 15 μm to about 60 μm, from about 15 μm to about 70 μm, from about 15 μm to about 80 μm, from about 15 μm to about 90 μm, from about 15 μm to about 100 μm, from about 20 μm to about 50 μm, from about 20 μm to about 60 μm, from about 20 μm to about 70 μm, from about 20 μm to about 30 μm, from about 20 μm to about 35 μm, from about 20 μm to about 40 μm, from about 20 μm to about 45 μm, about 5 μm, about 10 μm, about 15 μm, about 20 μm, about 25 μm, about 30 μm, about 35 μm, about 40 μm, about 45 μm, about 50 μm, about 55 μm, about 60 μm, about 65 μm, about 70 μm, about 75 μm, about 80 μm, about 85 μm, about 90 μm, about 100 μm, or about any values there between.

In some embodiments, wherein the one or more fluidic microchannels have a length of from about 0.1 mm to about 10 mm, from about 0.1 mm to about 0.5 mm, from about 0.1 mm to about 1 mm, from about 0.1 mm to about 2 mm, from about 0.1 mm to about 3 mm, from about 0.1 mm to about 4 mm, from about 0.1 mm to about 5 mm, from about 0.1 mm to about 6 mm, from about 0.1 mm to about 7 mm, from about 0.1 mm to about 8 mm, from about 0.1 mm to about 9 mm, from about 0.5 mm to about 1 mm, from about 0.5 mm to about 2 mm, from about 0.5 mm to about 3 mm, from about 0.5 mm to about 4 mm, from about 0.5 mm to about 5 mm, from about 0.5 mm to about 6 mm, from about 0.5 mm to about 7 mm, from about 0.5 mm to about 8 mm, from about 0.5 mm to about 9 mm, from about 0.5 mm to about 10 mm, from about 1 mm to about 2 mm, from about 1 mm to about 3 mm, from about 1 mm to about 4 mm, from about 1 mm to about 5 mm, from about 1 mm to about 6 mm, from about 1 mm to about 7 mm, from about 1 mm to about 8 mm, from about 1 mm to about 9 mm, from about 1 mm to about 10 mm, from about 2 mm to about 3 mm, from about 2 mm to about 4 mm, from about 2 mm to about 5 mm, from about 2 mm to about 6 mm, from about 2 mm to about 7 mm, from about 2 mm to about 8 mm, from about 2 mm to about 9 mm, from about 2 mm to about 10 mm, about 0.1 mm, about 0.2 mm, about 0.3 mm, about 0.4, about 0.5 mm, about 0.6 mm, about 0.7 mm, about 0.8 mm, about 0.9 mm, about 1 mm, about 1.5 mm, about 2.0 mm, about 2.5 mm, about 3.0 mm, about 3.5 mm, about 4.0 mm, about 4.5 mm, about 5.0 mm, about 5.5 mm, about 6.5 mm, about 7.5 mm, about 8.0 mm, about 8.5 mm, about 9.0 mm, about 10 mm, or any value there between.

In some embodiments, the distance between adjacent microchannels is from about 10 µm to about 500 µm, from about 25 µm to about 500 µm, from about 0.05 mm to about 0.5 mm, from about 0.05 mm to about 0.1 mm, from about 0.05 mm to about 0.15 mm, from about 0.05 mm to about 0.2 mm, from about 0.05 mm to about 0.25 mm, from about 0.05 to about 0.3 mm, from about 0.05 mm to about 0.35 mm, from about 0.05 mm to about 0.4 mm, from about 0.05 mm to about 0.5 mm, from about 0.1 to about 0.15 mm, from about 0.1 mm to about 0.2 mm, from about 0.1 mm to about 0.25 mm, from about 0.1 to about 0.3 mm, from about 0.1 mm to about 0.35 mm, from about 0.1 mm to about 0.4 mm, from about 0.1 mm to about 0.5 mm, about 0.05 mm, about 0.1 mm, about 0.15 mm, about 0.2 mm, about 0.25 mm, about 0.3 mm, about 0.35 mm, about 0.4 mm, about 0.5 mm, or any value there between.

Reaction Chambers

As used herein, a reaction chamber is referred to as a micro scale space at least partially enclosed by the materials of other components of the microfluidic devices or by its own wall(s) in a cell assay unit.

A reaction chamber connects fluidically with a micropocket and leak channel of a cell assay unit. In some embodiments, a reaction chamber further comprises two or more split bipolar electrodes. In some embodiments, a reaction chamber has a dimension of from about a few ten micrometers to about a few hundred micrometers of its width, height, and depth.

As used herein, the width of a reaction chamber is referred to the horizontal distance of the two points that are on the opposite edges of the cross section along the wall of the reaction chamber and are furthest away from each other. As used herein, the height or tallness of a reaction chamber is referred to the vertical distance of the points that are on the opposite edges of the cross section on the wall of the reaction chamber and are furthest away from each other. As used herein, the length of a reaction chamber is the shortest distance from the edge that the micropocket connects to the opposite edge.

A reaction chamber can have any shape as one skilled in the art can understand. The cross section of a reaction chamber can have any two-dimensional shape. In some embodiments, the cross section of a reaction chamber can be regular or irregular a square, rectangle, circle, or a combination thereof. In some embodiments, the cross section of a reaction chamber is a regular rectangle.

In some embodiments, the cross section of a reaction chamber is uniform along its entire length. In some other embodiments, the cross section of a reaction chamber is not uniform along its entire length.

In some embodiments, all reaction chambers are the same. In some other embodiments, one or some of the reaction chambers in a disclosed microfluidic device can be different from other reaction chambers in the same microfluidic device, in terms of their dimension, their connections with the leak channels/micropocket, number of the split BPEs, or combination thereof.

A reaction chamber can have a volume of from about 100 pL to about 10 nL, from about 100 pL to about 200 pL, from about 100 pL to about 300 pL, from about 100 pL to about 400 pL, from about 100 pL to about 500 pL, from about 100 pL to about 600 pL, from about 100 pL to about 700 pL, from about 100 pL to about 800 pL, from about 100 pL to about 900 pL, from about 100 pL to about 1,000 pL, from about 100 pL to about 1,000 pL, from about 100 pL to about 1,200 pL, from about 100 pL to about 1,400 pL, from about 100 pL to about 1,600 pL, from about 100 pL to about 1,800 pL, from about 100 pL to about 2,000 pL, from about 0.1 nL to about 1 nL, from about 0.5 nL to about 2 nL, from about 1 nL to about 2 nL, from about 1 nL to about 4 nL, from about 2 nL to about 5 nL, about 0.1 nL, about 0.2 nL, about 0.3 nL, about 0.4 nL, about 0.5 nL, about 0.6 nL, about 0.7 nL, about 0.8 nL, about 0.9 nL, about 1.0 nL, about 2.0 nL, about 3.0 nL, about 4.0 nL, about 5.0 nL, about 6.0 nL, about 7.0 nL, about 8.0 nL, about 9.0 nL, about 10.0 nL, or any value there between.

The reaction chamber is used in the microfluid devices disclosed herein to hold necessary compounds or reagents for any cell assay or characterization. The compounds, reagents, or solutions can be one of those for PCR or other cell analysis or characterization methods.

For example, once the captured cells are inside the reaction chambers, they can be subjected to single-cell qPCR or RT-qPCR analysis, which will target mutations and transcripts associated with invasiveness and resistance to drugs of the captured cells. With this approach, the distribution of a mutation by qPCR of individually captured cells can be quantified and one-pot RT-qPCR for parallel single-cell gene expression analysis can be carried out. Similarly, CTCs isolated from clinical samples can be analyzed to create a point-of-care assay to stratify patients, predict response to therapy, and track CTC subpopulations.

Another example to analyze and characterize the captured cells inside the reaction chambers is to determines invasive potential and the effectiveness of drugs targeted against CTC migration. This approach can utilize the distance migrated by each cell into a collagen matrix in the reaction chambers as an indicator of invasiveness. With this approach, CTCs derived from patients with metastatic melanoma can be analyzed and the impact of a drug on migration distance of the CTC cell can be monitored.

In some embodiments, a reaction chamber does not have one or two of its top wall(s).

In some other embodiments, the reaction chamber has a width of from about 50 µm to about 1,200 µm, from about 100 µm to about 1,000 µm, from about 100 µm to about 800 µm, from about 100 µm to about 600 µm, from about 100 µm to about 500 µm, from about 200 µm to about 1,000 µm, from about 200 µm to about 800 µm, from about 200 µm to about 600 µm, from about 200 µm to about 400 µm. In some other embodiments, the width of a reaction chamber is about 50 µm, about 100 µm, about 150 µm, about 200 µm, about 250 µm, about 300 µm, about 350 µm, about 400 µm, about 450 µm, about 500 µm, about 550 µm, about 600 µm, about 650 µm, about 700 µm, about 750 µm, about 800 µm, or about any value there between.

In some other embodiments, a reaction chamber has a height of from about 5 µm to about 100 µm from about 10 µm to about 100 µm, from about 5 µm to about 100 µm, from about 10 µm to about 15 µm, from about 10 µm to about 20 µm, from about 10 µm to about 25 µm, from about 10 µm to about 30 µm, from about 10 µm to about 35 µm, from about 10 µm to about 40 µm, from about 10 µm to about 45 µm, from about 10 µm to about 50 µm, from about 10 µm to about 55 µm, from about 10 µm to about 60 µm, from about 10 µm to about 70 µm, from about 10 µm to about 80 µm, from about 10 µm to about 90 µm, from about 15 µm to about 20 µm, from about 15 µm to about 25 µm, from about 15 µm to about 30 µm, from about 15 µm to about 35 µm, from about 15 µm to about 40 µm, from about 15 µm to about 45 µm, from about 15 µm to about 50 µm, from about 15 µm to about 60 µm, from about 15 µm to about 70 µm, from about 15 µm to about 80 µm, from about 15 µm to about 90 µm, from about 15 µm to about 100 µm, from about 20 µm to about 50 µm, from about 20 µm to about 60 µm, from about 20 µm to about 70 µm, from about 20 µm to about 30 µm, from about 20 µm to about 35 µm, from about 20 µm to about 40 µm, from about 20 µm to about 45 µm, about 5 µm, about 10 µm, about 15 µm, about 20 µm, about 25 µm, about 30 µm, about 35 µm, about 40 µm, about 45 µm, about 50 µm, about 55 µm, about 60 µm, about 65 µm, about 70 µm, about 75 µm, about 80 µm, about 85 µm, about 90 µm, about 100 µm, or about any values there between.

In some embodiments, wherein a reaction chamber has a length of from about 25 µm to about 1,000 µm, from about 100 µm to about 1,000 µm, from about 100 µm to about 800 µm, from about 100 µm to about 600 µm, from about 100 µm to about 500 µm, from about 200 µm to about 1,000 µm, from about 200 µm to about 800 µm, from about 200 µm to about 600 µm, from about 200 µm to about 400 µm. In some other embodiments, the width of a reaction chamber is about 50 µm, about 100 µm, about 150 µm, about 200 µm, about 250 µm, about 300 µm, about 350 µm, about 400 µm, about 450 µm, about 500 µm, about 550 µm, about 600 µm, about 650 µm, about 700 µm, about 750 µm, about 800 µm, or about any value there between.

Leak Channels

As used herein, a leak channel is referred to as a microfluidic passage between a reaction chamber and a microchannel. A leak channel is different from a micropocket within a cell assay unit and can be considered an outlet for the fluid going through the reaction chamber, while the micropocket can be considered as inlet of the fluid going through the reaction chamber. However, in some embodiments of the devices or methods disclosed herein, the flow direction can be reversed, i.e., the leak channel can be used as an inlet for a fluid going through a reaction chamber and the micropocket can be used as an outlet for a fluid going into the reaction chamber.

In some embodiments, a leak channel has a dimension of from about a few micrometers to about a few hundred micrometers of its width, height, and depth.

As used herein, the width of a leak channel is referred to the horizontal distance of the two points that are on the opposite edges of the cross section along the flow direction and are furthest away from each other. As used herein, the height or tallness of a leak channel is referred to the vertical distance of the points that are on the opposite edges of the cross section along the flow direction. As used herein, the length of a leak channel is the shortest distance from the edge that the reaction chamber to the edge that connect the microchannel.

The cross section of a leak channel can have any shape as one skilled in the art can understand. The cross section of a leak channel can have any two-dimensional shape. In some embodiments, the cross section of a leak channel can be regular or irregular a square, rectangle, circle, or a combination thereof. In some embodiments, the cross section of a leak channel is a regular rectangle.

In some embodiments, the cross section of a leak channel is uniform along its entire length. In some other embodiments, the cross section of leak channel is not uniform along its entire length.

In some embodiments, a leak channel connects with a reaction chamber at an angle of from about 15° to 90°. In some other embodiments, a leak channel connects with a microchannel at an angle of from about 15° to 90°.

In some embodiments, all leak channels are the same. In some other embodiments, one or some of the leak channels in a disclosed microfluidic device can be different from other leak channels in the same microfluidic device, in terms of their dimension, their connections with the reaction chambers/microchannels, or combination thereof.

In some embodiments, a leak channel does not have one or two of its top wall(s).

In some other embodiments, a leak channel has a width of from about 5 µm to about 50 µm, from about 5 µm to about 10 µm, from about 5 µm to about 15 µm, from about 5 µm to about 20 µm, from about 5 µm to about 25 µm, from about 5 µm to about 30 µm, from about 5 µm to about 35 µm, from about 10 µm to about 35 µm, from about 10 µm to about 30 µm, from about 10 µm to about 25 µm, from about 15 µm to about 20 µm, from about 15 µm to about 25 µm, from about 20 µm to about 25 µm, about 5 µm, about 10 µm, about 15 µm, about 20 µm, about 25 µm, about 30 µm, about 35 µm, about 40 µm, about 45 µm, about 50 µm, or about any values there between.

In some other embodiments, a reaction chamber has a height of from about 5 µm to about 100 µm from about 10 µm to about 100 µm, from about 5 µm to about 100 µm, from about 10 µm to about 15 µm, from about 10 µm to about 20 µm, from about 10 µm to about 25 µm, from about 10 µm to about 30 µm, from about 10 µm to about 35 µm, from about 10 µm to about 40 µm, from about 10 µm to about 45 µm, from about 10 µm to about 50 µm, from about 10 µm to about 55 µm, from about 10 µm to about 60 µm, from about 10 µm to about 70 µm, from about 10 µm to about 80 µm, from about 10 µm to about 90 µm, from about 15 µm to about 20 µm, from about 15 µm to about 25 µm, from about 15 µm to about 30 µm, from about 15 µm to about 35 µm, from about 15 µm to about 40 µm, from about 15 µm to about 45 µm, from about 15 µm to about 50 µm, from about 15 µm to about 60 µm, from about 15 µm to about 70 µm, from about 15 µm to about 80 µm, from about 15 µm to about 90 µm, from about 15 µm to about 100 µm, from about 20 µm to about 50 µm, from about 20 µm to about 60 µm, from about 20 µm to about 70 µm, from about 20 µm to about 30 µm, from about 20 µm to about 35 µm, from about 20 µm to about 40 µm, from about 20 µm to about 45 µm, about 5 µm, about 10 µm, about 15 µm, about 20 µm, about 25 µm, about 30 µm, about 35 µm, about 40 µm, about 45 µm, about 50 µm, about 55 µm, about 60 µm, about 65 µm, about 70 µm, about 75 µm, about 80 µm, about 85 µm, about 90 µm, about 100 µm, or about any values there between.

In some embodiments, wherein a reaction chamber has a length of from about 25 µm to about 1,200 µm, from about 25 µm to about 1,100 µm, from about 25 µm to about 1,000 µm, from about 100 µm to about 1,000 µm, from about 100 µm to about 800 µm, from about 100 µm to about 600 µm, from about 100 µm to about 500 µm, from about 200 µm to about 1,000 µm, from about 200 µm to about 800 µm, from about 200 µm to about 600 µm, from about 200 µm to about 400 µm. In some other embodiments, the length of a leak channel is about 50 µm, about 100 µm, about 150 µm, about 200 µm, about 250 µm, about 300 µm, about 350 µm, about 400 µm, about 450 µm, about 500 µm, about 550 µm, about 600 µm, about 650 µm, about 700 µm, about 750 µm, about 800 µm, about 900 µm, about 950 µm, about 1,000 µm, about 1,100 µm, about 1,200 µm, about 1,250 µm, about 1,300µ, or about any value there between.

Microfluidic Devices

In some embodiments, the one or more arrays of the cell assay units are placed along the one or more fluidic microchannels. In some embodiments, the one or more fluidic microchannels have a width of from about 5 µm to about 200 µm, a height of from about 5 µm to about 100 µm, and a length of from about 0.1 mm to about 20 mm.

In some other embodiments, the one or more fluidic microchannels have a width of from about 50 µm to about 120 µm, a height of from about 20 µm to about 60 µm, and a length of from about 1 mm to about 10 mm.

In some embodiments, the one or more fluidic microchannels have two or more side walls, one or more bottom walls, one or more top walls, one or more circular walls, or a combination thereof. In some other embodiments, the one or more fluidic microchannels are rectangular shaped fluidic microchannels and have two side walls and one bottom wall.

In some embodiments, the one or more arrays of the cell assay units are placed along the bottom wall(s) of or inside the one or more fluidic microchannels.

In some embodiments, the microfluidic device comprises 8, 16, 32, 64, 128 or 256 of the fluidic microchannels. In some other embodiments, each of one or more fluidic microchannels is separated from another adjacent microchannel by a distance from about 50 µm to about 500 µm.

In some embodiments, the two or more microchannels are grouped together by fluidic connection at their respective end and then connect to another group of microchannels. In some other embodiments, the two or more microchannels are merged together into a bigger channel or reservoir.

In some embodiments, the cell assay units reside inside side, bottom, top, circular wall(s), or a combination thereof of the one or more fluidic microchannels. In some embodiments, the cell assay units reside inside both side walls of the one or more fluidic microchannels.

In some embodiments, the reaction chamber has a regular or irregular cubic, rectangular, or ball shape.

In some embodiments, the reaction chamber has a volume of from about 100 pL to about 10 nL.

In some embodiments, the reaction chamber is of cubic or rectangular shape and has a width of from about 50 µm to about 1,200 µm, a length of from about 25 µm to about 1,000 µm, and a height of from about 5 µm to about 100 µm. In some other embodiments, the reaction chamber is of cubic or rectangular shape and has a width of from about 100 µm to about 300 µm, a length of from about 200 µm to about 400 µm, and a height of from about 15 µm to about 30 µm.

In some embodiments, the reaction chamber is fluidically connected to the micropocket and the leak channel. In some other embodiments, the reaction chamber is fluidically connected to the micropocket at an angle of from about 15 to 90°. In yet some other embodiments, the reaction chamber is fluidically connected to the leak channel at an angle of from about 15 to 90°.

In some embodiments, the cross-section of the micropocket has a regular or irregular square, rectangular, or circular shape. In some other embodiments, the micropocket has a width of from about 1 µm to about 200 µm, a length of from about 10 µm to about 100 µm, and a height of from about 5 µm to about 100 µm. In yet some other embodiments, the micropocket has a width of from about 5 µm to about 100 µm, a length of from about 50 µm to about 100 µm, and a height of from about 15 µm to about 30 µm.

In some embodiments, the micropocket has an opening to the fluidic microchannel and another opening to the reaction chamber of the same cell assay unit. In some other embodiments, the micropocket is straight or curved.

In some embodiments, the cross-section of the leak channel has a regular or irregular square, rectangular, or circular shape. In some other embodiments, the leak channel has a width of from about 5 µm to about 50 µm, a length of from about 50 µm to about 1,200 µm, and a height of from about 5 µm to about 100 µm.

In some other embodiments, the leak channel has a width of from about 5 µm to about 25 µm, a length of from about 50 µm to about 1,000 µm, and a height of from about 15 µm to about 30 µm.

In some other embodiments, the leak channel is straight or curved.

In some embodiments, the cell assay unit comprises a BPE in its micropocket. In some other embodiments, the cell assay unit comprises a BPE in its micropocket and the BPE has a distance of from about 50 µm to about 40 µm from the tip of the BPE to the edge of the microchannel.

In some embodiments, the cell assay unit comprises a BPE at the bottom of the micropocket.

In some embodiments, the cell assay unit further comprises two or more split BPEs inside the reaction chamber. In some embodiments, the cell assay unit further comprises two split BPEs inside the reaction chamber.

In some embodiments, one reaction chamber is away from its adjacent reaction chamber in the same array by a distance from about 5 µm to about 500 µm, measured from one edge of one reaction chamber to the closest edge of the reaction chamber.

In other embodiments, one array of the cell assay units is away from its adjacent array of reaction chamber by a distance of from about 20 µm to about 1,000 µm, measured from one edge of reaction chamber in one array to its closest end of another reaction chamber in the adjacent array.

In some embodiments, the bipolar electrode has one or two triangular ends. In some other embodiments, the bipolar electrode has a circular tip at one or two of its ends. In some embodiments, the end of the bipolar electrode inside the micropocket is from about 5 µm to about 40 µm away from the edge of the closest fluidic microchannel.

In some embodiments, the wall(s) of the fluidic microchannels, reaction chambers, micropockets, or leak channels comprise polydimethylsiloxane, polymethylmethacrylate (PMMA), a polymeric material, glass material, or a combination thereof.

In some embodiments, the wireless bipolar electrode comprises an electric conductor or semiconductor.

In some embodiments, the bipolar electrode has a width from about 1 µm to about 50 µm, a thickness from about 1 µm to about 50 µm, a length from about 10 µm to about 1,000 µm, or combination thereof.

In some embodiments, the micropocket in a microfluidic device have different dimensions or sizes, to accommodate a need to capture cells of different sizes, kinds, or other properties. A microfluidic device disclosed herein can have a distribution of various micropockets for different separations or purposes.

In some embodiments, the ends of the bipolar electrodes is from about 10 µm to about 40 µm, from about 5 µm to about 35 µm, from about 8 µm to about 12 µm, from about 5 µm to about 20 µm, from about 8 µm to about 15 µm, about 5 µm, about 8 µm, about 10 µm, about 12 µm, about 15 µm, about 20 µm, about 25 µm, about 30 µm, about 35 µm, about 40 µm, or any value there between away from the edge of the closest fluidic microchannel or the opening of the microchambers in which the bipolar electrodes reside.

In some embodiments, the distance between two adjacent split bipolar electrodes is from about 0.5 µm to about 500 µm, from about 1 µm to about 500 µm, from about 2 µm to about 500 µm, from about 5 µm to about 500 µm, from about 10 µm to about 500 µm, from about 10 µm to about 100 µm, from about 10 µm to about 50 µm, from about 5 µm to about 15 µm, from about 8 µm to about 12 µm, from about 20 µm to about 500 µm, from about 20 µm to about 100 µm, from about 20 µm to about 50 µm, about 0.5 µm, about 1 µm, about 2 µm, about 5 µm, about 8 µm, about 10 µm, about 12 µm, about 20 µm, about 30 µm, about 40 µm, about 45 µm, about 35 µm, about 50 µm, about 60 µm, about 70 µm, about 80 µm, about 90 µm, about 100 µm, about 110 µm, about 120 µm, about 130 µm, about 140 µm, about 150 µm, about 160 µm, about 170 µm, about 180 µm, about 190 µm, about 200 µm, about 210 µm, about 230 µm, about 250 µm, about 270 µm, about 290 µm, about 300 µm, about 320 µm, about 340 µm, about 360 µm, about 380 µm, about 400 µm, about 420 µm, about 440 µm, about 460 µm, about 480 µm, about 500 µm, or about any value there between. This distance is from one tip of one bipolar electrode to its closest tip of another electrode.

In some embodiments, the microfluidic device further comprises a power source that is configured to have electrical communication with the ionically conductive solution and to supply an AC electric field to the ionically conductive solution.

In some embodiments, the microfluidic device is configured to generate an electric field around both ends of each bipolar electrode by capacitive charging of the electrical double layer induced at the ends of the bipolar electrode by an AC voltage only. In some other embodiments, the microfluidic device is configured to cause no faradaic reaction at both ends of the bipolar electrode by any DC voltage.

In some embodiments, the microfluidic device is configured to produce an electric field maximum in the ionically conductive solution near both ends of the bipolar electrode electrical double layer by capacitive charging of the electrical double layer induced at the ends of the bipolar electrode by an AC voltage only.

In some embodiments, the power source is configured to supply an AC with a frequency range from about 1 kHz to about 100 MHz. In some other embodiments, the power source is configured to supply an AC with a voltage range from about 1 V to about 1 kV.

In the microfluidic devices disclosed herein, the desired AC voltage and frequencies are usually supplied by a device capable for delivering such AC voltage or frequencies, such as an AC or AC/DC power supply, with or without waveform generator. In the microfluidic devices disclosed here, not every electrode are connected to the power supply. Only are the last column of electrodes (at each outer edge of the device) interconnected to a single electrical lead (driving electrode), respectively. The power supply or power source is connected to these two leads (driving electrodes).

In some embodiments, the walls of the microfluidic channels comprise a polymeric material. In some embodiments, the walls of the microfluidic channels comprise polydimethylsiloxane, polymethylmethacrylate (PMMA), glass or the like.

In some embodiments, the walls of the microchambers comprise a polymeric material. In some embodiments, the walls of the microchambers comprise polydimethylsiloxane, polymethylmethacrylate (PMMA), glass or the like.

In some embodiments, the wireless bipolar electrode comprises an electric conductor, semiconductor, or a combination thereof. In some other embodiments, the wireless bipolar electrode comprises conductive material or semiconductive material. In yet another embodiment, the wireless bipolar electrode comprises conductive elemental metal, elemental gold, elemental platinum, elemental copper, carbon, metal oxide, indium tin oxide, or a combination thereof. In yet another embodiment, the wireless bipolar electrode comprises semi-conductive material, boron-doped diamond, or n-doped or p-doped silicon, or a combination thereof.

In some embodiments, the bipolar electrode has a width of from about 1 µm to about 50 µm, or any value there between. In some embodiments, the bipolar electrode has a thickness of from about 1 µm to about 50 µm, or any value there between. In yet some other embodiments, the bipolar electrode has a length of from about 10 µm to about 1,200 µm (1.2 mm), or any values there between. In some embodiments, the bipolar electrode has length of from about 0.1 mm to about 1.1 mm, or any values there between. In some other embodiments, the bipolar electrode has a circular cross section and a diameter of from about 5 µm to about 50 µm or any value there between.

In some embodiments, the power source comprises a waveform generator and amplifier.

In another aspect, the present disclosure provides a system for isolating and analyzing or characterizing a specific cell, wherein the system comprises a microfluidic device disclosed herein and an ionically conductive solution.

In another aspect, the present disclosure provides a method for isolating and analyzing or characterizing a cell from a biological matrix using one device. The method comprises contacting a biological sample with an ionically conductive solution in a fluidic device disclosed herein and applying an AC electric field to the bipolar electrodes in the micropockets for a period of time so a targeted cell is trapped at the tip of the bipolar electrode inside the micropocket; wherein the targeted cell is subsequently transferred to a reaction chamber for analysis or characterization, and wherein the biological sample contains the targeted cell to be isolated.

In some embodiments, the ionically conductive solution has a conductivity from about 1 mS/m (milli-Siemens per meter, wherein a Siemen is the inverse of an Ohms) to about 1 S/m, from about 1 mS/m to about 10 mS/m, from about 1 mS/m to about 50 mS/m, from about 1 mS/m to about 100 mS/m, from about 1 mS/m to about 200 mS/m, from about 1 mS/m to about 300 mS/m, from about 1 mS/m to about 400 mS/m, from about 1 mS/m to about 500 mS/m, from about 1 mS/m to about 600 mS/m, from about 1 mS/m to about 700 mS/m, from about 1 mS/m to about 800 mS/m, from about 1 mS/m to about 900 mS/m, from about 10 mS/m to about 50 mS/m, from about 10 mS/m to about 100 mS/m, from about 10 mS/m to about 200 mS/m, from about 10 mS/m to about 300 mS/m, from about 10 mS/m to about 400 mS/m, from about 10 mS/m to about 500 mS/m, from about 10 mS/m to about 600 mS/m, from about 10 mS/m to about 700 mS/m, from about 10 mS/m to about 800 mS/m, from about 10 mS/m to about 900 mS/m, from about 50 mS/m to about 100 mS/m, from about 50 mS/m to about 200 mS/m, from about 50 mS/m to about 300 mS/m, from about 50 mS/m to about 400 mS/m, from about 50 mS/m to about 500 mS/m, from about 50 mS/m to about 600 mS/m, from about 50 mS/m to about 700 mS/m, from about 50 mS/m to about 800 mS/m, from about 50 mS/m to about 900 mS/m, including any ranges there between.

As used herein, a biological sample is any sample taken from a live system or derived from a sample taken from a live system. The biological sample as used here is referred to as any collection of samples containing multiple live cells. The biological sample as used herein includes blood or plasma samples taken from an animal or samples that are processed by other procedures but originated from blood or plasma.

As used herein, a target cell is one that can undergo dielectrophoresis.

In some embodiments, the one or more wireless electrodes are in one or more microchambers, respectively.

In some embodiments, the contacting is to flow the biological sample through the one or more fluidic channel of the fluidic device.

In some embodiments, the method further comprises turning off the AC electric field to transfer the targeted cell from the micropocket to the reaction chamber. In some other embodiments, the method further comprises turning on and then turn off alternatively.

In some embodiments, the method further comprises washing the one or more fluidic microchannels with an ionically conductive solution. In some embodiments, the ionically conductive solution is an ionic liquid. In yet some other embodiments, the ionically conductive solution is 1-Decyl-3-methylimidazolium bis(trifluoromethanesulfonyl)imide.

In some embodiments, the method further comprises exchanging the ionically conductive solution with a solution suitable for cell analysis or characterization. In some other embodiments, the method further comprises exchanging the ionically conductive solution with a second solution suitable for cell analysis or characterization, and then exchanging the second solution with another ionically conductive solution. In some embodiments, the another ionically conductive solution is an ionic liquid. In yet some other embodiments, the another ionically conductive solution is 1-Decyl-3-methylimidazolium bis(trifluoromethanesulfonyl)imide. This another ionically conductive solution prevents the cells in different cell assay units from mixing with each other and allows the cells in different cell assay units analyzed or characterized separately. In some other embodiments, the ionic liquid is a cross-linkable ionic liquid. The compounds in a cross-linkable ionic liquid can cross-link with each other upon exposure to heat or UV light. Use of a cross-linkable ionic liquid can seal the reaction chambers and "lock in place" the captured cells or lysed cells inside the reaction chambers, after the cross-linkable ionic liquid is introduced and the cross-linking is initiated.

In some embodiments, the method further comprises washing the one or more fluidic microchannels with an ionically conductive solution when the AC electric field is on.

In some embodiments, the method further comprises lysing the targeted cell inside the reaction chamber, using an electric field between the split BPEs.

In some embodiments, the targeted cell is a circulating tumor cell (CTC).

In some other embodiments, the biological matrix is a blood sample.

In some embodiments, the ionically conductive solution has a linear flow velocity or flow rate of from about 0 µm/s to about 120 µm/s, about 0.1 µm/s to about 120 µm/s, about 0.1 µm/s to about 80 µm/s, from about 5 µm/s to about 110 µm/s, from about 10 µm/s to about 100 µm/s, from about 15 µm/s to about 105 µm/s, from about 20 µm/s to about 100 µm/s, from about 25 µm/s to about 95 µm/s, from about 30 µm/s to about 90 µm/s, from about 25 µm/s to about 95 µm/s, about 20 µm/s, about 30 µm/s, about 35 µm/s, about 40 µm/s, about 45 µm/s, about 50 µm/s, about 55 µm/s, about 60 µm/s, about 65 µm/s, about 70 µm/s, or any value there between.

In some embodiments, the AC electric field applied in the fluidic device is a series of AC electric fields with different frequencies and voltages. In some embodiments, the targeted cell undergoes a positive DEP response. In some other embodiments, the targeted cell undergoes a negative DEP response.

In some other embodiments, the method has throughput of from about 0.01 mL/h to about 30 mL/h, from about 0.01 mL/h to about 0.5 mL/h, from about 0.01 mL/h to about 1 mL/h, from about 0.01 mL/h to about 2 mL/h, from about 0.01 mL/h to about 4 mL/h, from about 0.01 mL/h to about 6 mL/h, from about 0.01 mL/h to about 8 mL/h, from about 0.01 mL/h to about 10 mL/h, from about 0.01 mL/h to about 12 mL/h, from about 0.01 mL/h to about 14 mL/h, from about 0.01 mL/h to about 16 mL/h, from about 0.01 mL/h to about 18 mL/h, from about 0.01 mL/h to about 20 mL/h, from about 0.01 mL/h to about 22 mL/h, from about 0.01 mL/h to about 24 mL/h, from about 0.01 mL/h to about 26 mL/h, from about 0.01 mL/h to about 28 mL/h, from about 0.1 mL/h to about 0.5 mL/h, from about 0.1 mL/h to about 1 mL/h, from about 0.1 mL/h to about 2 mL/h, from about 0.1 mL/h to about 4 mL/h, from about 0.1 mL/h to about 6 mL/h, from about 0.1 mL/h to about 8 mL/h, from about 0.1 mL/h to about 10 mL/h, from about 0.1 mL/h to about 12 mL/h, from about 0.1 mL/h to about 14 mL/h, from about 0.1 mL/h to about 16 mL/h, from about 0.1 mL/h to about 18 mL/h, from about 0.1 mL/h to about 20 mL/h, from about 0.1 mL/h to about 22 mL/h, from about 0.1 mL/h to about 24 mL/h, from about 0.1 mL/h to about 26 mL/h, from about 0.1 mL/h to about 28 mL/h, from about 0.1 mL/h to about 30 mL/h, from about 0.5 mL/h to about 0.5 mL/h, from about 0.5 mL/h to about 1 mL/h, from about 0.5 mL/h to about 2 mL/h, from about 0.5 mL/h to about 4 mL/h, from about 0.5 mL/h to about 6 mL/h, from about 0.5 mL/h to about 8 mL/h, from about 0.5 mL/h to about 10 mL/h, from about 0.5 mL/h to about 12 mL/h, from about 0.5 mL/h to about 14 mL/h, from about 0.5 mL/h to about 16 mL/h, from about 0.5 mL/h to about 18 mL/h, from about 0.5 mL/h to about 20 mL/h, from about 0.5 mL/h to about 22 mL/h, from about 0.5 mL/h to about 24 mL/h, from about 0.5 mL/h to about 26 mL/h, from about 0.5 mL/h to about 28 mL/h, or from about 0.5 mL/h to about 30 mL/h, including any ranges there between, of the biological matrix.

In some other embodiments, the method has throughput of from about 1 mL/h to about 30 mL/h, from about 1 mL/h to about 2 mL/h, from about 1 mL/h to about 5 mL/h, from about 1 mL/h to about 10 mL/h, from about 1 mL/h to about 15 mL/h, from about 1 mL/h to about 20 mL/h, from about 1 mL/h to about 25 mL/h, from about 1 mL/h to about 50 mL/h, including any ranges there between, of the biological matrix.

In some other embodiments, the method has throughput about 0.01 mL/h, about 0.02 mL/h, about 0.05 mL/h, about 0.08 mL/h, about 0.1 mL/h, about 0.2 mL/h, about 0.4 mL/h, about 0.6 mL/h, about 0.8 mL/h, about 1 mL/h, about 2 mL/h, about 3 mL/h, about 4 mL/h, about 5 mL/h, about 6 mL/h, about 8 mL/h, about 10 mL/h, about 12 mL/h, about 14 mL/h, about 16 mL/h, about 18 mL/h, about 20 mL/h, about 22 mL/h, about 24 mL/h, about 26 mL/h, about 28 mL/h, or about 30 mL/h, including any ranges there between, of the biological matrix.

Significantly, the disclosed microfluidic devices communicate an AC field across insulating barriers (microchannel walls) thus enabling the simultaneous capture cells, such as CTCs, across parallel microchannels. The micropockets aligned to the BPE tips and embedded along the wall of each microchannel provide discreet capture sites with defined volume, thus enabling single-cell capturing or with an additional selection based on size of the microchambers or other attributes (length, spacing, shape, distribution of BPEs and microchannels, and etc.) for the BPEs, microchannels, microchambers, power source, or a combination thereof. Moreover, the use of wireless electrodes removes the need to provide ohmic contact to each electrode, thus simplifying the device design and fabrication process. This feature provides unparalleled flexibility for DEP schemes that access large sample volumes along all axes. Finally, the disclosed invention can isolate and fully release captured cells and to retain cell viability at the same time, a requirement for the downstream analysis of cells, such as culturing and testing of drug efficacy. The disclosed devices prove to be useful in further studies centering upon the selective capture of CTCs from blood for the establishment of diagnosis and prognosis of cancer and for the evaluation of anticancer therapies.

Furthermore, the wireless BPEs with the triangular ends and round tips as used in some of the disclosed microfluidic devices also made it possible to capture a single cell or microemboli of cells and to have more wireless electrodes in the same footprint.

The current disclosure has demonstrated that the integration of wireless electrodes allows for the creation of DEP microfluidic devices that are easily scalable along the x- and y-directions, which increases throughput.

Furthermore, due to the incorporation of a reaction chamber, micropocket, leak channel, and split BPEs into the disclosed microfluidic devices, single-cell capture, transfer into the reaction chamber for lysis and other characterization or analysis was readily achieved by adjusting the size of microchambers to the size of the targeted cells, turning AC on or off, and adjusting AC voltage alone. In fact, the sizes of the microchambers, shapes or tips of the BPEs, and/or other parameters in a microfluidic device disclosed herein do not have to be uniform and can be different to capture a cell or microemboli of cells. For example, in a preferred embodiment, a microfluidic device can be configured to capture single cells upstream, but capture microemboli of the same cells downstream, by using the different sizes for the microchambers. In another preferred embodiment, the microfluidic device can be configured to capture multiple cells, which can be accomplished by capturing single cells repeatedly and aggregating them to achieve a desired cluster of cells. Other attributes of the microchannels, microchambers, BPEs, voltage and frequency of the AC field, or a combination thereof can also be adjusted to avoid capturing a single cell, to capture single cells or microemboli of cells, or anything in between, for various purposes.

Similarly, the length and spacing between them do not have to be uniform in an open-channel microfluidic device disclosed herein. In fact, the length and spacing of the BPEs are important factors for capturing cells or microemboli of cells.

The disclosed microfluidic devices exhibit significant advancements in DEP technology including wireless control of the AC field and enhanced design flexibility, which led to increased throughput and high-fidelity parallel single-cell capture. These advancements are made while retaining the inherent advantages of DEP including selective and label-free isolation of cells and ease of fabrication, which provide an avenue to utilize the disclosed microfluidic devices for point-of-care applications, not only as a result of its ability to isolate single CTC cells, but also as a result of its flexibility to capture other type of cells or mixture of multiple cells. The captured cells can be isolated, accumulated, and then used for its characterizations, such as its invasiveness and response to various drugs all within the same device. The microfluidic devices disclosed herein have potential clinic applications, such as for accurate disease diagnosis and selection of effective treatment, all within a single chip.

Live and Lysed Cell Assays

Beyond quantification (e.g., capture efficiency, purity), specific assays need to be conducted to bridge the gap between the laboratory and the clinic. Use of a dielectrophoresis (DEP) technique with the microfluidic device described herein allows high cell viability to be maintained during capture and release of CTCs, whereas optionally, trapped CTCs can be electrically lysed. Thus, it is possible to perform assays for live CTCs or for their cellular contents. Live-cell imaging provides dynamic information of cell behavior, which renders it applicable for in situ monitoring of motility in response to the local microenvironment. Such migration data may elucidate the factors that influence the invasiveness of CTCs.

Live Cell Assay

Probing the Role of Multicellular Organization in Three-Dimensional Environments Cellular signaling is often altered for tumor cells cultured on flat substrates that lack of structural cues. For this reason, much emphasis has been placed over the past few decades in technical advances to develop in vitro 3D modules to mimic in vivo systems. 3D systems that embed cells or cell spheroids within tissue-like hydrogels rely on slow spontaneous aggregation of spheroids and possess poorly controlled size and shape of those aggregates. Beneficially, the microfluidic device and methods described herein can be used to address the slowness of existing methods.

Lysed Cell Assay

The Enzymatic Activity of Intracellular-β-Galactosidase

Assays of cellular contents present sources for resolving the static heterogeneity of CTCs. The discrimination of distinct levels of a protein or a gene is of high value in understanding the growth and division of carcinoma cells. Enzymatic assay, such as probing the intracellular β-galactosidase activity, provides insights into cell senescence, in which proliferation of malignant cells does not occur. Thus, intracellular β-galactosidase may be used as an indicator for testing the efficiency of chemotherapeutic agents. Likewise, single-cell PCR is powerful in identifying somatic mutations such as KRAS or BRAF. Consequently, customized therapies can be exploited.

While all steps needed for single-cell assays are configured in the current design, further modifications are necessary to suit customized assays. For example, picoliter microchambers are favorable for enzymatic assays, while much larger volumes (normally, nanoliter scale) are required for single-cell PCR.

All publications, patent applications, issued patents, and other documents referred to in this specification are indicative of the level of ordinary skill in the art to which this invention pertains and are herein incorporated by reference to the same extent as if each individual publication or patent application was specifically and individually indicated as incorporated by reference. Definitions that are contained in text incorporated by reference are excluded to the extent that they contradict definitions in this disclosure.

The present invention is further illustrated by the following examples, which should not be considered as limiting in any way.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Chemicals and Cell Culture

Chemicals

The silicone elastomer and curing agent (Sylgard 184), bovine serum albumin (BSA) (biotech grade), and 0.25% Trypsin-EDTA (1×) were purchased from Fisher Scientific (Thermo Fisher Scientific, Inc., Waltham, Mass.). The DMEM/F12 cell culture medium, dextrose (d-glucose), sucrose, Pluronic® F-108, 1.0 M Tris•HCl stock and the ionic liquid 1-Decyl-3-methylimidazolium bis(trifluoromethanesulfonyl)imide were obtained from Sigma-Aldrich, Inc. (St. Louis, Mo.). All dilutions were conducted with Type 1 water (18.2 MΩ·cm). DEP buffer was comprised of 8.0% sucrose, 0.3% dextrose, and 0.1% BSA in 1.0 mM Tris buffer (pH=8.1).

Cell Culture

MDA-MB-231 cells were obtained from ATCC and cultured in DMEM/F12 with 1% pen-strep and 10% fetal bovine serum supplementation at 37° C. and 5% $CO_2$. All cells were sub-cultured every 2 days to maintain a cell confluence less than 80%. In preparation of DEP experiments, MDA-MB-231 cells were detached from culture flask using 0.25% Trypsin-EDTA (1×), followed by pelleting by centrifugation (1100 rpm, 5 min) and resuspension in 7.0 mL Tris DEP buffer. Pelleting and resuspension to cell concentration of $5 \times 10^3$ cells/mL was repeated to wash cells twice in DEP buffer before DEP capture experiments.

DEP Experiments.

All the devices were designed to operate such that the MDA-MB-231 cell solutions were flowed through the fluidic microchannel, from which they were attracted to and captured at BPE tips (pDEP). Device operation was accomplished by the application of an AC voltage at coplanar driving electrodes at each side of the BPE arrays using a Tektronix AFG3011C waveform generator (Tektro-nix, Beaverton, Oreg.) and Trek model 2205 amplifier (Trek, Lockport, N.Y.). The AC frequency was maintained at 70 kHz at which MDA-MB-231 cells experience strong pDEP. A Nikon Eclipse Ti inverted microscope and Nikon AZ-100 microscope (Nikon, Tokyo, Japan) were utilized to image cells to obtain fluorescence and bright field images, respectively.

Device Dimensions.

The dimensions for the exemplary designs presented in this disclosure are described here. All microchannels, micropockets, and reaction chambers are 25 μm tall. A reaction chamber is 200 μm wide and 400 μm long. A leak channel, whose length and width can be different in the each of the Examples below, was affixed at 60° C. to each chamber to make a fluidic connection to the fluidic microchannel. The exemplary microfluidic devices used in the following Examples have two parallel fluidic microchannels. The main parallel microchannels were each 6.8 mm long×100 μm wide×25 μm tall and separated by 1.05 mm (center-to-center). Each side of each parallel fluidic microchannel featured 12 cell-assay units (micropocket, reaction chamber, and leak channel), leading to 48 units in total. The BPEs inside the micropockets have a distance of 5 μm from the fluidic microchannel. The two rows of electrodes at the ends (outermost channels) were interconnected and led to contacts for the waveform generator.

Although the microfluidic devices used in this Example section have two fluidic microchannels, the number of the cell assay units can be readily increased in both x- and y-directions by using increase the number of the fluidic microchannels and of the cell assay units along each fluidic microchannel. The scalability of the microfluidic devices disclosed herein permits parallel sampling and analysis of large input volumes, while the whole device is controlled by only two driving electrodes. The high-throughput capability is of great importance in search for rare cell events. The exemplary microfluidic device shown in this Examples section has 2 parallel channels in a footprint of 15.6 $mm^2$. If the device was scaled to 2,210 $mm^2$, a device with up to 280 parallel channels with over 2,800 chambers would be anticipated. Assuming 1-100 CTCs/mL CTC concentration in whole blood, the scaled device can process at least 28 mL blood, without exhausting the reaction chambers. Further, the current device is flexible in functions. The split BPE design has dual functions in the firm retention of live single cells and electric lysis, thus allowing assays of single live cells and intracellular contents to be exploited. Additionally, DEP-based technique is high selective and non-invasive, which could also be applied for other mammalian cells and bacteria. In summary, the present BPE array-based DEP design provide alternative approaches in single cell profiling, and the advancements demonstrated such as valve-free manipulation and integration for single cell analysis can be envisioned to advance the understanding of cellular events for point-of-care applications.

Example 1

Design of the Cell Assay Units in the Microfluidic Devises Disclosed Herein

In the existing microfluidic devices disclosed in U.S. patent application Ser. No. 15/793,587 for capturing single cells, cell-scale micropockets extruding from either side of microchannels ensure individual cells to be selectively captured at each BPE tip.

In the microfluidic devices disclosed herein, reaction chambers are introduced adjacent to the micropockets for isolation and store a necessary amount of reagent solution for single cell assay.

Figure 4A:
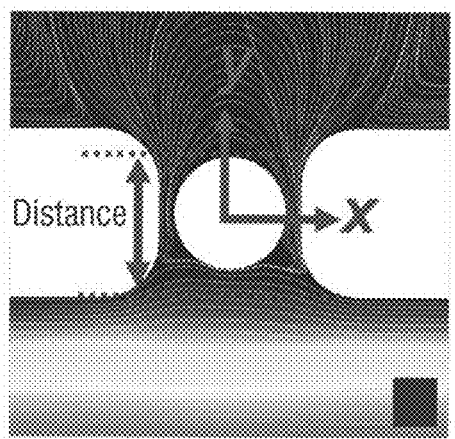
FIG. 4A-FIG. 4D show the results of the cell transfer step in the absence of a leak channel.
Figure 4B:
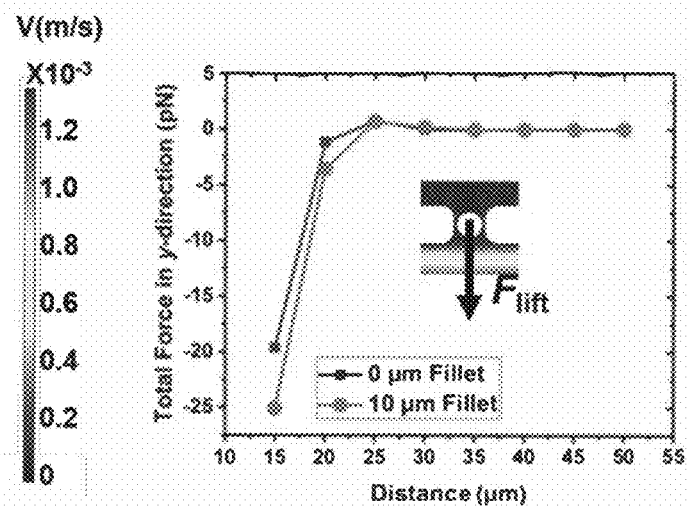
Figure 4C:
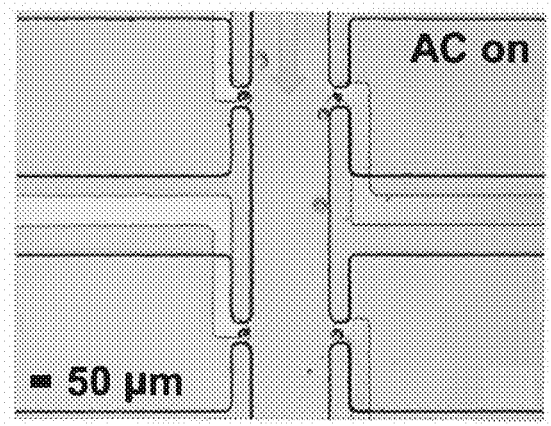
Figure 4D:
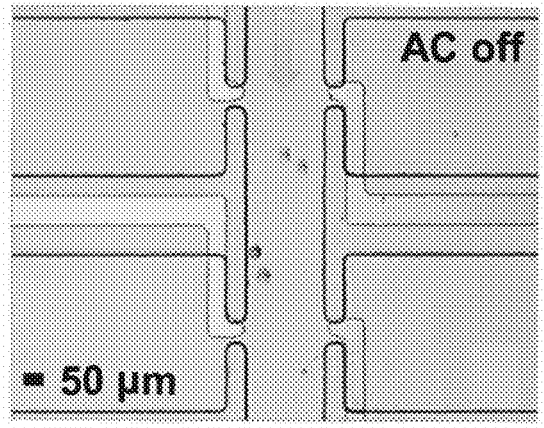

Transfer of each cell from a micropocket to its adjacent reaction chamber can be accomplished by increasing contact area between cells and reagents. FIG. 4A-FIG. 4D show the results of the cell transfer step in the absence of a leak channel. FIG. 4A shows a simulated contour plot for the flow velocity and streamlines of the device when a cell (represented by a white circle) is captured in the pocket. For this simulation, all pocket corners are filleted by 10 µm. FIG. 4B shows a numerical simulation of the total force experienced by a cell along the y-direction as a function of the distance of the far edge of a cell to the fluidic microchannel. The inlet velocity of the fluidic microchannel was set to 100 µm/s. FIG. 4C and FIG. 4D show the experimental results of cell captured and transfer when AC is on and off, respectively. The grey arrows represent the flow direction.

As shown in FIG. 4A, in the y-direction, the cell experiences lift force (pressure force, towards fluidic microchannel) and drag force (viscous force, towards chamber), while in the x-direction, only drag force is exerted on the cell. Positive total force along the y-direction is therefore required for the forward movement into reaction chambers. FIG. 4B is the computed result of the total force ($F_{Total}$) exerted on a cell when it is located in the micropocket and the reaction chamber has no additional fluidic connection (i.e., no leak channel). The x-axis, as depicted in FIG. 4A, is the distance of a cell from the fluidic microchannel opening. FIG. 4C and FIG. 4D are sequential bright field images and show the result of turning off the AC voltage after cell capture. This result show that in the absence of a leak channel, the drag force along the y-direction is negligible and the lift force created by fluid flow can easily pull the cell out of the pocket. Additionally, a rounded pocket corner can enhance lift force, and thereby impedes cell transfer. Consequently, sharp pocket corners are desired, or an additional force is required to push cells forward into the reaction chambers.

Figure 5A:
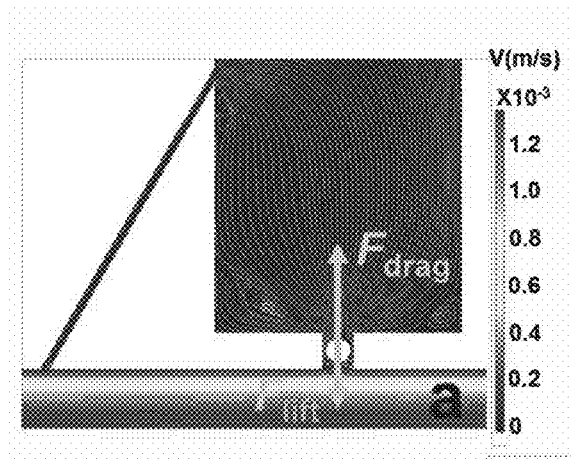
FIG. 5A-FIG. 5E show the results of the cell transfer step when a leak channel is added to each reaction chamber.

The required additional force to move the captured cells from micropockets to reaction chambers is provided by the leak channels that connecting the fluidic microchannels to the reaction chambers. A leak channel introduces an additional drag force perpendicular to the fluidic microchannel by forming a flow pathway into the micropocket and out of the leak channel as shown in FIG. 5A. Thus, when two flow pathways are present, cells experience an additional drag force ($F_{Drag}$) created by leak flow along the y-direction. Consequently, when an electric field is applied, cells of interest can be selectively captured at the micropockets; and then, after turning off the AC voltage, captured single-cells move along the leak flow circuit, and are transferred into the reaction chambers.

To achieve the desired capture and transfer of individual cells, several parameters need to be considered. The first parameter is the micropocket size. Micropockets enable volumetric control of the number of cells captured and protect cells from being washed away by fluid flow. To perform single-cell capture, cell-scale pockets are required.

The second parameter is leak channel width. A large leak channel cross section leads to fast flow (strong $F_{Drag}$), which pushes cells into reaction chambers even when the AC capture voltage is on and results in capture of multiple cells. Furthermore, under this condition, cells randomly circle in and out of the reaction chambers. On the other hand, if the leak channel width is too narrow, extremely fast flow is needed for cell transfer, and inconveniently, two distinct flow rates would be required for the capture step (slow flow) and transfer step (fast flow). Thus, the leak channel width needs to lie between these extremes.

The third parameter is BPE location. Since the position of the captured cell determines the relative strength of drag forces derived by the two flow pathways (along fluidic microchannel and along leak channel), and thereby the direction of cell movement, the location of the BPE tip must be carefully controlled. When cells are captured within fluidic microchannel streamlines, the cells are readily knocked away by fluid flow. However, when BPE tips are far away from fluidic microchannels, cell transfer becomes very favorable but may lead to attachment of a second cell.

Figure 5B:
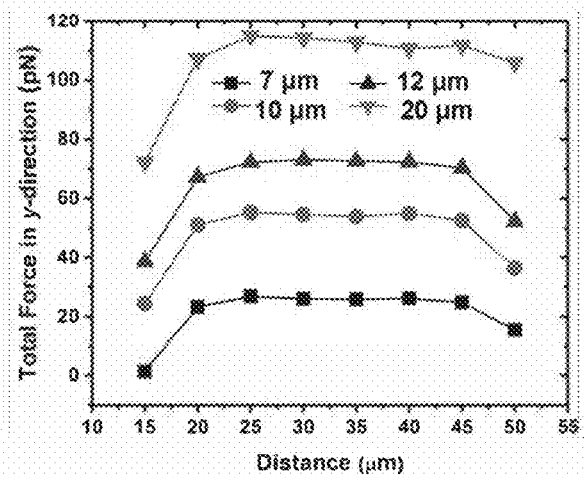
Figure 5C:
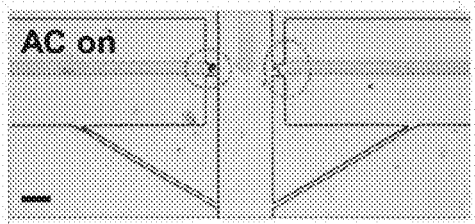
Figure 5D:
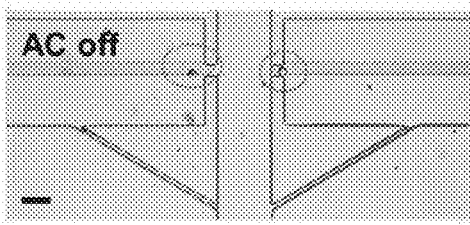
Figure 5E:
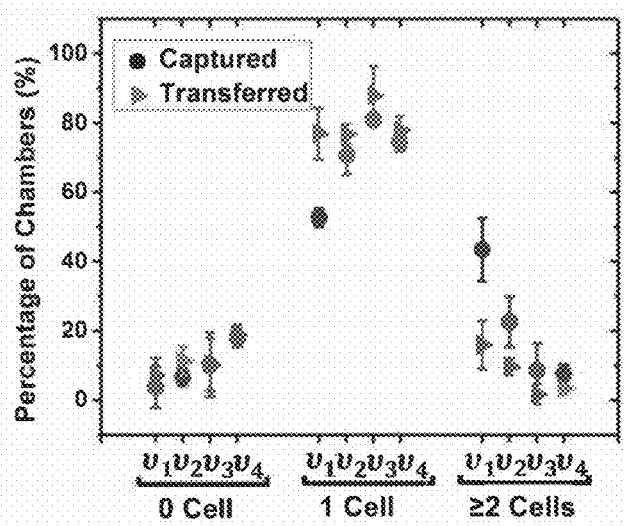

FIG. 5A-FIG. 5E show the results of the cell transfer step when a leak channel is added to each reaction chamber. FIG. 5A shows the simulated contours of the flow velocity and streamlines of the device when a cell is captured in the pocket. FIG. 5B shows the corresponding numerical simulation results of the total force experienced by a cell along the y-direction when varying leak channel width is 7 µm, 10 µm, 12 µm, and 20 µm, respectively. The x-axis represents the distance of a cell to the fluidic microchannel. For FIG. 5A and FIG. 5B, the inlet velocity of the fluidic microchannel was set to 100 µm/s. FIG. 5C and FIG. 5D show the experimental results of cell captured and transfer when AC is on and off, respectively. The applied voltage was kept at 14 Vpp at 70 kHz. FIG. 5E shows the optimization of cell capture and transfer performance as a function of the average linear velocity of the fluidic microchannel. The $v_1$-$v_4$ represent the average linear velocity of 80, 100, 120, and 150 µm/s, respectively. Scale bar is 50 µm.

To investigate the influence of the leak channel width and BPE location on cell transfer performance, total force ($F_{Lift}$ and $F_{Drag}$) exerted on captured cells was computed using COMSOL simulation software (Multiphysics 5.2a, COMSOL, Inc., Burlington, Mass.). As shown in FIG. 5A, a 20 µm spherical particle was chosen to represent a typical MDA cell. Total force ($F_{Total}$) was computed as a function of the distance (d) of a particle to the fluidic microchannel opening. The resultant $F_{Total}$ in the x-direction ($F_{Total-x}$) indicates the spin status of a cell, while $F_{Total}$ in the positive y-direction ($F_{Total-y}$) suggests the forward movement of cells into reaction chambers. FIG. 5B shows the impact on these forces when d is varied for several different leak channel widths. Based on these results, it can be concluded that $F_{Total-y}$ is very sensitive (and $F_{Total-x}$, insensitive) to leak channel resistance, which increases exponentially with decreasing hydraulic radius. For instance, increasing leak channel width from 7 µm to 10 µm results in an increase of ~30 pN (about 10 pN per micron) for $F_{Total-y}$. The increase in $F_{Total-y}$ is more modest when further widening the leak channel from 20 µm (~0.62 pN per micron). The strong $F_{Total-y}$ obtained with leak widths exceeding 10 µm is on the order of the DEP capture force and explains experimental results in which cells were continuously transferred into the chamber even when the capture voltage was applied. Hence, a leak channel with a 7 µm opening was chosen. Additionally, a distance (d) of 25-35 µm (placing the cell completely inside the pocket) prevents the cell from being washed away without compromising capture efficiency. It was found experimentally that this capture position was best achieved with a BPE tip positioned 5-15 µm inside the pocket.

Using this optimized design, MDA cells were successfully captured individually at each electrode tip when the AC capture voltage was on, and subsequently transferred into reaction chambers after turning off the AC voltage as shown in FIG. 5C and FIG. 5D.

To obtain optimal capture and transfer performance, the effect of flow rate was also evaluated. FIG. 5E shows the percentage of empty (0 cells), singly occupied (1 cell), and multiply occupied (≥2 cells) micropockets/chambers as quantified during capture and transfer steps and as a function of average linear flow velocity in the fluidic microchannel. To obtain this result, first, a Pluronic-treated device was rinsed with DEP buffer for 15 min. Second, an AC signal (14 $V_{pp}$, 70 kHz) was applied at the driving electrodes to generate the average electric field strength ($E_{avg,rms}$) of 24.74 kV/m. The solution in the inlet reservoir was then replaced with cell solution, and a height differential was established between the inlet and outlet reservoirs to achieve a desired fluid flow in the trapping channels. After cell trapping for 5 min, two separate sets of images were taken with AC voltage on and then off for quantification of cell capture and transfer, respectively. Subsequently, the number of cells at each pocket and in each reaction chamber was carefully counted. As shown in FIG. 5E, increasing flow rate from 80 µm/s to 120 µm/s reduced multi-cell capture, while going further to 150 µm/s, empty micropockets significantly increased, leading to a decrease in the percentage of single-cell capture. At 120 µm/s, excellent single cell capture (81.2%) and transfer (88.0%) were achieved. Therefore, 120 µm/s was chosen for subsequent experiments. Additionally, the results of FIG. 6E demonstrate that the present design is advantageous for transferring single cells. At 80 µm/s, 43.4% of pockets had multiple cells captured, while only 15.8% had two or more cells transferred into chambers. Consequently, the chance of having single cells in each chamber further increases after cell transfer. These results are significant because they demonstrate the valve-free capture and transfer of individual breast cancer cells in a scalable DEP device at an array of wireless electrodes.

Example 2

Split BPE Design For Selective Recapturing and Retention of Individual Cells.

The leak channel design has successfully enabled capture and transfer of individual cells into reaction chambers. To integrate on-chip molecular analysis of single cells, the firm retention of isolated cells in the confined microstructures is crucial, especially in the case when fluid exchange is required. To address such demand, a split BPE design in which each single BPE employed previously was divided into two separate BPEs was developed as shown in FIG. 6A-FIG. 6F.

FIG. 6A-FIG. 6F show results of the cell re-capture step using split BPEs, time lapse images of cell capture, transfer, and recapture accomplished by only turning on and off the applied voltage. FIG. 6A shows cells flowing through channels when AC was off. FIG. 6B shows that turning on AC resulted in single-cell capture. FIG. 6C and FIG. 6D show that turning AC back off and then on enabled cell transfer and re-capture at the tips of the split BPEs. FIG. 6E and FIG. 6F show that captured cells were released and re-captured when AC was again turned off and then on. The applied voltage for all images was 22 Vpp at 70 kHz with average flow velocity of 120 µm/s. FIG. 6G shows the optimization of applied voltage for cell capture and transfer when split BPEs were employed. Scale bar is 50 µm.

Consequently, cells transferred into reaction chambers could be attracted and firmly retained at the split BPEs. The distinct split BPE design exhibits triple advantages: First, only cells that experience pDEP can be re-captured and lysed, which further enhances selective trapping of target cells. Second, the DEP-based technique allows marker-free isolation and retains high cell viability. Third, fast fluid exchange can be conducted via both convection and diffusion since cells transferred are held in place by split BPEs. Thus, selective isolation of live single cells, transfer and position into a designated container, followed by maintenance of cell viability and fluid exchange can be exploited. It is worth noting that conventional single-cell isolation methods (i.e. serial dilution, mouth pipet, and laser-capture micro-dissection) are often plagued by time spent, operational complexity, deterioration of cell viability, and inability to select a specific type of cells. However, the microfluidic device using a leak channel and a split BPE is rapid, highly efficient, and easy-to-operate for unbiased selection of individual cells. The simplicity in manufacturing and the robustness of isolation make it attractive for live cell assays to be characterized for mechanistic studies of cell heterogeneity.

Another compelling attribute of this split BPE design is the ability to create highly localized electric field maxima, thus allowing fast electrical lysis without modification of channels or addition of further electrical leads. For assays including genomics and proteomics, of importance is lysis of cells to release intracellular contents. Considering the potential alteration of a target molecule's native structure and expression during lysis, the lysis approach must be both gentle and rapid. Traditional mechanical lysis such as bead beating is effective on the macroscale but not compatible with a microfluidic device. Although sharp nanostructures have been reported for cell lysis in microchannels, inclusion of such structures greatly complicates device fabrication. Sonication typically takes about 50 s for single cell lysis and the heat generated may denature proteins. Chemical lysis, often with detergents, is a potentially milder and quicker protocol, while it requires precise liquid handling (an extra fluid exchange step) and careful selection of optimal lysis media. Electrical lysis, achieved by placing cells under sufficiently high electric field for electroporation, is simple, fast, and efficient. To avoid the formation of gas bubbles under a high electric field, AC electric field is often employed. While a large variety of lysis methods are reported in microfluidics, integration of cell lysis with other function blocks to make a complete diagnostic system remains rare.

The split BPE design permits lysis of cells by simply increasing the AC electric field after cell re-capture at the BPE tips. Considering that breaking of a single BPE into two individual BPEs gives rise to an additional potential drop in the gap, a higher voltage is necessitated to achieve cell capture. Using the split BPE design, cells did not respond at 14 $V_{pp}$. Therefore, the applied voltage was increased to evaluate the optimal voltage in split BPE device. FIG. 6G shows the resulting cells per chamber that were captured under higher applied voltages of 18, 22, and 26 $V_{pp}$ and transferred (voltage off) while maintaining the optimized average flow velocity of 120 µm/s. At 18 $V_{pp}$, 23.3% of micropockets were empty, while this number dropped to 5.4% after increasing the capture voltage to 22 $V_{pp}$. A further increase to 26 $V_{pp}$ resulted in 100% of pockets being filled.

However, at this elevated voltage, the percentage of chambers containing multiple cells dramatically increased from 10.6% to 43.1%. Based on these results, 22 $V_{pp}$ was selected as the optimal voltage to achieve single-cell capture (84.4%) and transfer (89.4%) in the split BPE design. As shown in FIG. 6A-FIG. 6F, after cell transfer is achieved with the AC field 'off', turning it 'on' again causes cells to be re-directed towards the split BPE and re-captured in the gap. These results are significant because they demonstrate the ability of a split BPE to recapture an individual cell inside the chamber while maintaining a high success rate for single cell capture. Such recapture can allow retention of the cell during fluid exchange and position for electrical lysis.

Example 3

Optimizing Cell Lysis

After cells were re-captured at the split BPEs, electric lysis was performed by increasing the applied voltage. To ensure rapid and gentle lysis, 5 s was initially chosen, and a voltage were applied and increased gradually until all the cells were lysed. Prior to cell lysis, the fluid flow in the fluidic microchannels was stopped to observe the static lysis. FIG. 7A-FIG. 7J show the results of using split BPEs inside the reaction chamber and a higher voltage to optimize cell lysis.

FIG. 7A and FIG. 7C show the bright field images of the cells re-captured at split BPEs. FIG. 7B and FIG. 7D show the captured cells moved to the center of the split BPEs after the voltage were increased to 166 Vpp to initiate lysis for 1 second. FIG. 7E, and FIG. 7H show the fluorescent images of the captured single MDA-MB-231 cells (green). FIG. 7F and FIG. 7I show the fluorescent images after the lysis of the captured single MDA-MB-231 cells after AC field application for 5 seconds. FIG. 7G, and FIG. 7J show the changes of fluorescence intensity before and after lysis.

Upon electroporation, cell membrane was disrupted, and cells were expanded, which is consistent to previous report. It was found that lysis occurred when the voltage was increased to 112 $V_{pp}$, while 100% of cell lysis was achieved when increased to 166 $V_{pp}$. To further prove 166 $V_{pp}$ is the optimal condition, the applied voltage was directly increased from 22 Vpp to 166 $V_{pp}$ and maintained for 5 s. 100% of lysis was observed under the optimized condition. The non-uniform lysis at from 112 $V_{pp}$ to 166 $V_{pp}$ was observed and could be attributed to the heterogeneous size distribution.

Cells with small diameter have a higher threshold field strength for electroporation. Small cells were mainly retained at one BPE tip and gapped to another BPE tip. Therefore, the actual electric field experienced by small cells was mainly generated from one electrode. In contrast, large cells touched the tips of both split BPEs, thereby the electric field strength from both electrodes became dominant. Furthermore, cells with larger diameter require lower field strength threshold for electroporation. It is also worth noting that the gap between split BPEs plays a crucial role in fast lysis, since the electric field decays rapidly with distance (E=V/d). Consequently, close split BPEs maximize the electric field strength in between, and favor cell lysis at low applied voltage.

Figure 7K:
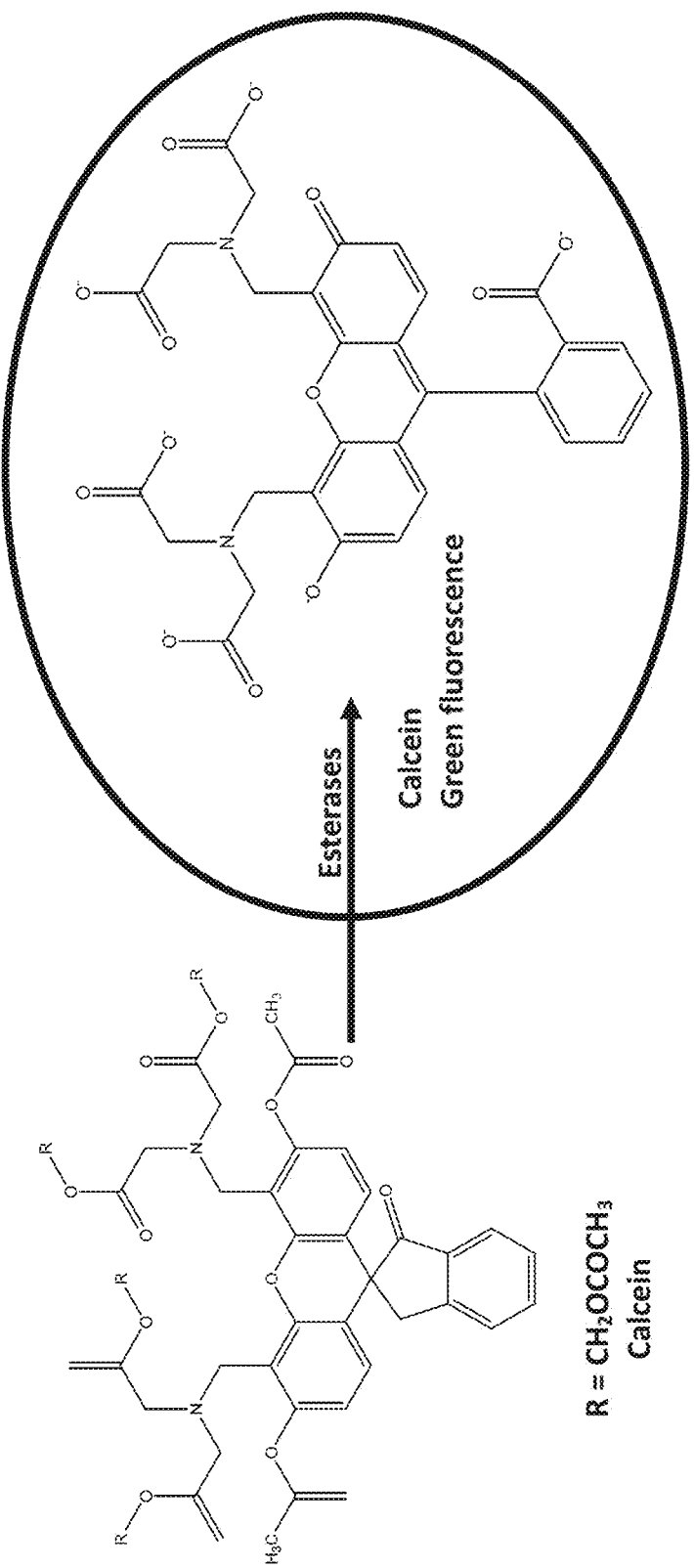
FIG. 7K is a graphical depiction of the relationship between Calcein outside of a live cell and in a live cell.
Figure 8A:
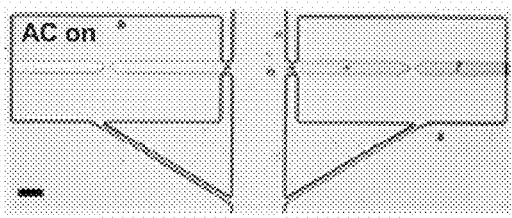
FIG. 8A-FIG. 8L show the bright-field images at each experimental step for single-cell profiling, the workflow of selection, fluid exchange, transfer, re-capture of individual MDA cells, and fluid isolation.
Figure 8B:
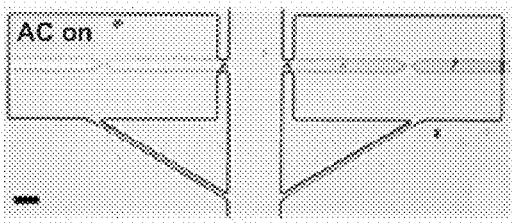
Figure 8C:
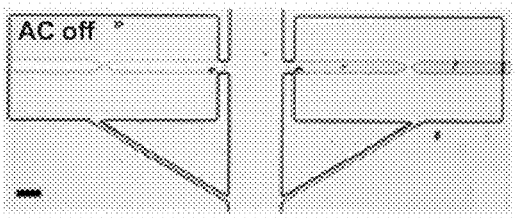
Figure 8D:
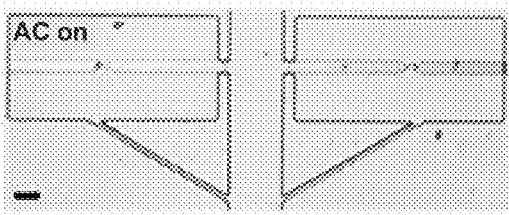
Figure 8E:
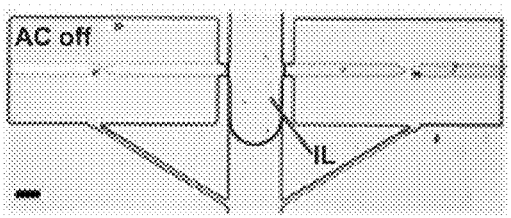
Figure 8F:
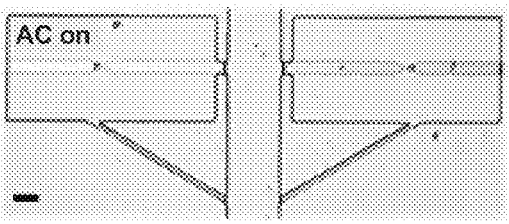
Figure 8G:
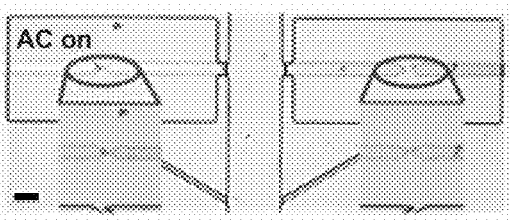
Figure 8H:
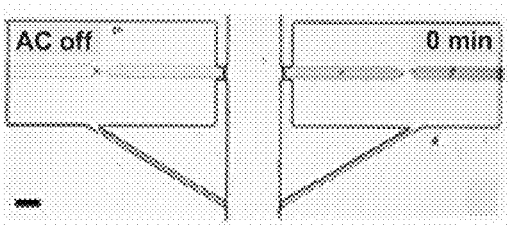
Figure 8I:
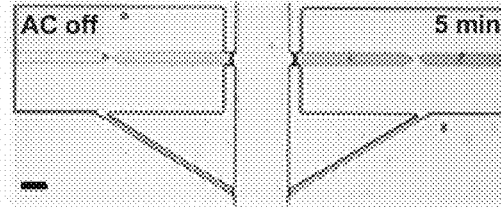
Figure 8J:
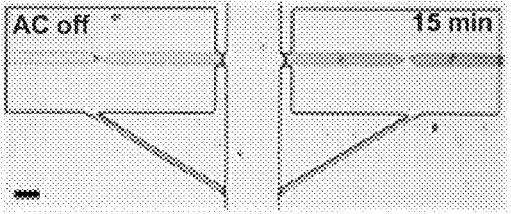
Figure 8K:
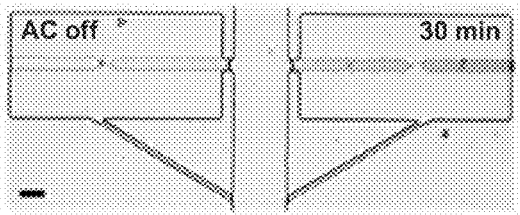
Figure 8L:
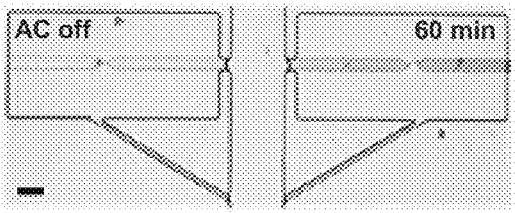

To further confirm that the electroporation occurred under 166 $V_{pp}$ for 5 s, MDA-MB-231 cells into which a membrane-permeant dye Calcein AM were delivered were used for demonstration. Non-fluorescent Calcein AM can be readily taken up into a cell and converted by the intracellular esterase enzymes into Calcein, which complexes calcium ions to generate a strong green fluorescence. Upon electroporation, cell membrane is disrupted, leading to the leakage of Calcein to the outside of cells and decrease of fluorescence intensity. FIG. 7K shows the relationship between Calcein and the cell.

Upon electroporation, the fluorescence intensity immediately decreased, which indicates membrane disruption and Calcein leakage. FIG. 7G and FIG. 7J. show that the fluorescent intensities decreased after 5 second AC voltage application, indicating the captured cells were lysed. DEP buffer solution contains 8.0% sucrose, 0.3% dextrose, 1.0 mM Tris pH 8.0 (6.2 mS/m).

After increasing the electric field, the fluorescent intensity was immediately decreased, which indicated the membrane disruption and Calcein leakage. Meanwhile, the intracellular contents were gradually diffused into the reaction chambers. Notably, the volume of the reaction chamber (2.0 nL) can be readily tuned to meet the requirements for various other assays. For instance, only increasing the depth from 25 μm to 84.4 μm results in a 6.75 nL reaction chamber, the smallest chambers used in the BioMark 96.96 dynamic arrays for single-cell RT-qPCR. Likewise, simply decreasing the chamber width and length by 4-fold each leads to a chamber with 125 pL, the same volume of microwells reported in single-cell RT-PCR of human B cell hybridomas. Since minimizing reaction volumes is critical for precise measurements on limited template, while the concentrations of target cell contents vary, the versatility in adjusting reaction chambers, which features in current design, is desired for a wide range of biochemical assays.

Example 4

Fluid Isolation by Ionic Liquid For Inhibiting Cross-Contamination While Retaining the Capability of Electrical Lysis The leak channel permits capture and transfer of individual cells into the reaction chambers, while the split BPEs allow retention and electrical lysis of cells for a variety of molecular assays inside the reaction chambers. Considering that cross-talk of adjacent chambers may affect the accurate readout during cellular characterizations, fluid isolation of each individual reaction chambers is crucial.

In the applications of live cell assays, digitalization of each compartments could be conducted using the mixture of traditional mineral oils and surfactants. However, to integrate the assays of cellular contents in the microfluidic devices disclosed herein, the isolation fluid must be conductive to enable cell lysis. Moreover, the fluid is desired to be hydrophobic, be thermally stable, and exhibit modest viscosity for liquid handling. Most importantly, the aqueous/non-aqueous boundary needs to be stable throughput assay monitoring. These requirements were met by choosing the ionic liquid 1-Decyl-3-methylimidazolium bis(trifluoromethanesulfonyl)imide as the isolation material for its high hydrophobicity, low viscosity, and high thermal stability. The ionic liquid's structure is shown below.

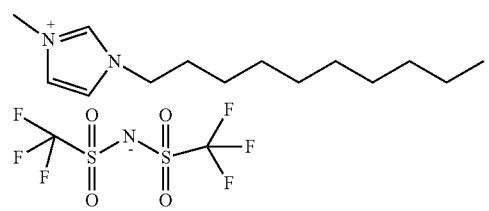

Various flow patterns and flow rates were evaluated to achieve the optimal fluid isolation. It was found that continuous flow at 0.1 μL/min allowed maintaining of the fluid boundary for at least 1 h without any propagation of ionic liquid into chambers. This result is significant because it demonstrates the potential of fluid isolation using ionic liquid for on-chip single cell analysis.

To further verify the robustness of current technique for single-cell profiling, the workflow of selection, fluid exchange, transfer, re-capture of individual MDA cells and fluid isolation were conducted. FIG. 8A-FIG. 8L show the bright-field images of each experimental step. To obtain such results, the present device was first treated using Pluronic solution overnight followed by rinsing with DEP buffer for 15 min. Then, 20 µL of cell solution was then dripped on the 1 mm reservoir and injected into the microchannels by using negative pressure. Under the optimal flow rate and applied electric field, over 90% of micropockets had single cells captured after ~15 min. Pure DEP buffer was next injected to wash away all the cells flowing through the microchannels. Subsequently, the applied voltage was turned off and back on to enable cell transfer and re-capture at the split BPE tips. At last, ionic liquid was introduced into each microchannels to avoid any cross-contamination of reaction chambers. By employing the current approach, single cells were successfully separated and isolated at each reaction chamber with stable fluid isolation after 1 h. These results are significant because they demonstrate the integration of single-cell capture, transport and isolation with parallel lysis for analysis in one standalone microfluidic device. Therefore, the microfluidic devices disclosed here not only meet the challenge of selective isolation of rare cells but also of on-chip analysis of the captured cells in a high-throughput and easy-to-operate manner.

Example 5

Comparing Fluid Exchange Efficiency of an Exemplary Microfluidic Device Disclosed Herein with a Similar Device Without a Leak Channel The leak channel permits capture and transfer of individual cells into the reaction chambers, while the split BPEs allow retention and electrical lysis of cells for a variety of molecular assays inside the reaction chambers. To investigate the efficiency of fluid exchange, the diffusions of a red dye in an exemplary microfluidic device and in a similar microfluidic device without a leak channel were monitored by fluorescence. FIG. 9A-FIG. 9D show the results obtained from exchange of the solutions of two different fluorescent dyes in DEP buffer in a microfluidic device without leak channels.

Specifically, 10 µL of the green dye solution was first pipetted in the 2.0 mm-diameter reservoir and injected into the microchannels by using negative pressure. The flow was then set to 0.1 µL/min and maintained for 30 min. Subsequently, the green dye solution in the reservoir was pipetted out and replaced with 10 µL of the red dye solution. Then, fluorescence images were obtained at multiple time points (up to 1 h) after starting the solution exchange.

The red dye used in this Example is 70 kDa dextran tagged with Texas Red. The red dye should have a representative diffusion coefficient of a large biomolecule that may be incorporated into a reagent mixture for a bioassay. On the other hand, the green dye is a small molecule and should diffuse more rapidly than the red dye.

Figure 9A:
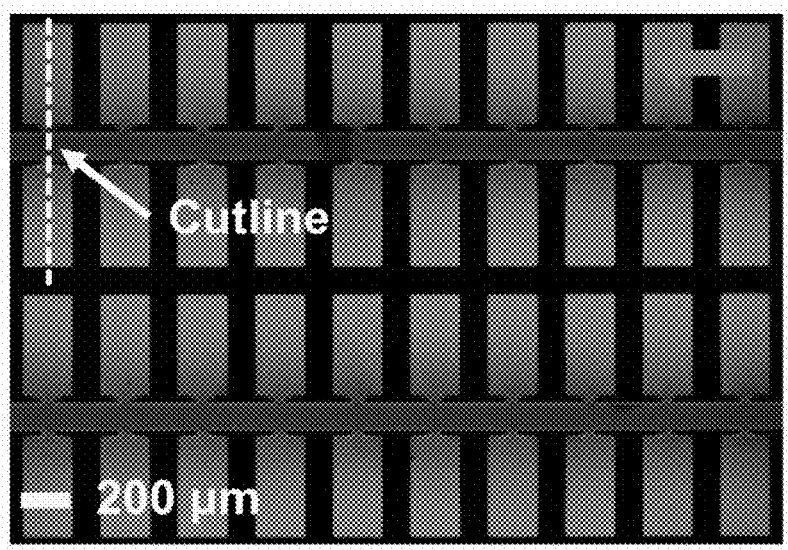
FIG. 9A-FIG. 9D show the fluorescence micrographs and diffusion profiles of a red dye in a microfluidic device without leak channel that was filled with a green dye.
Figure 9B:
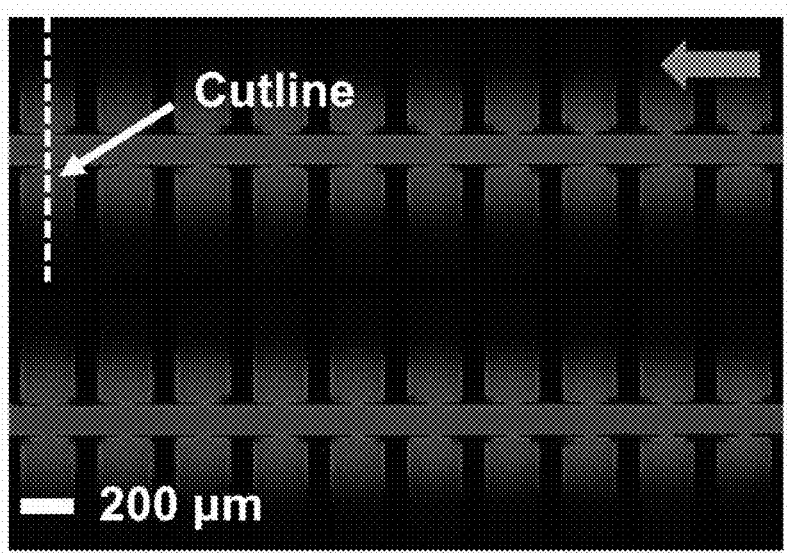
Figure 9C:
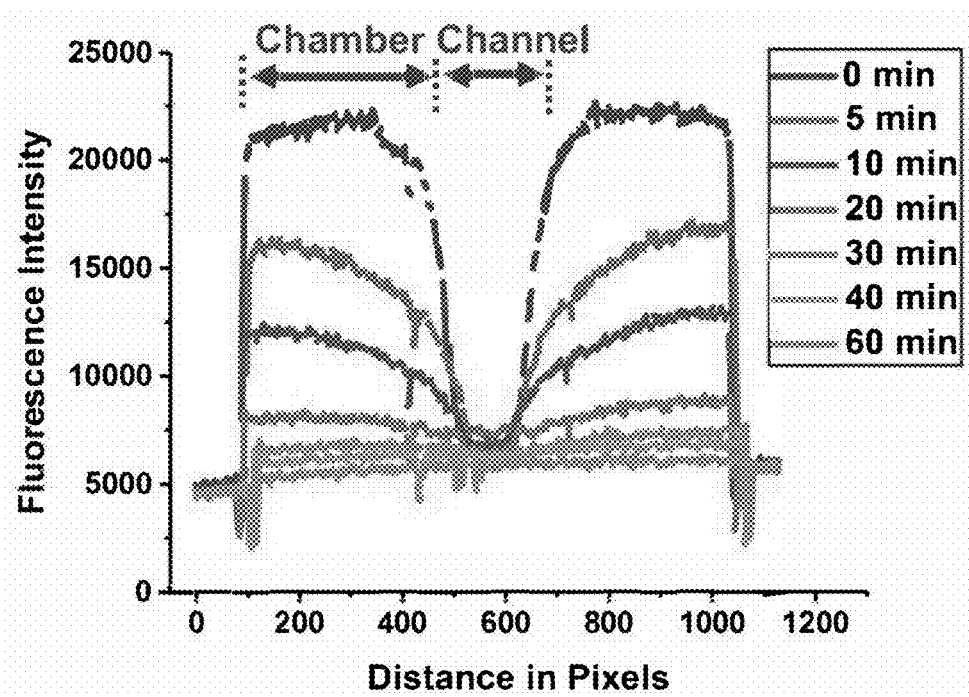
Figure 9D:
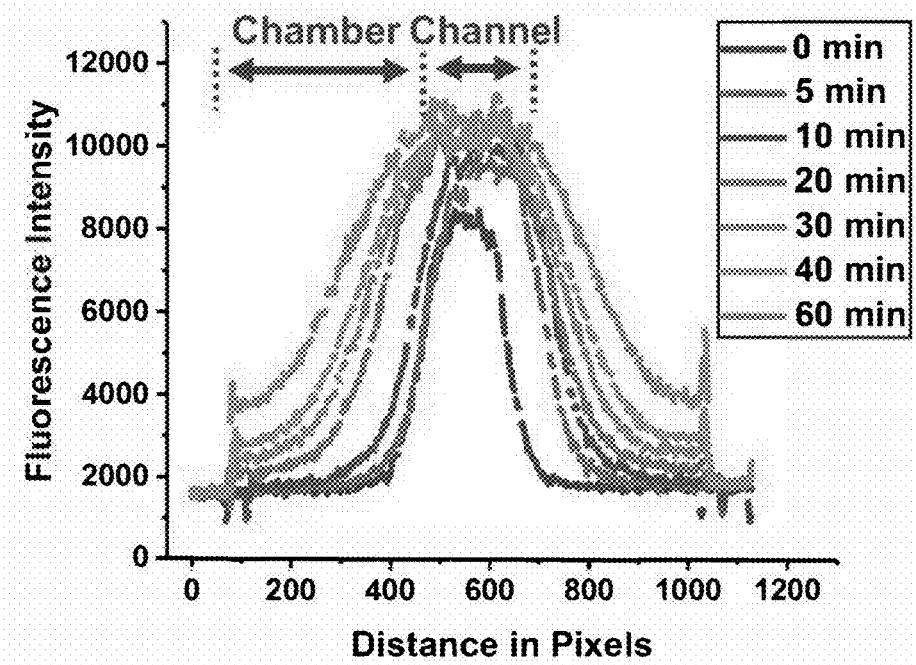

FIG. 9A shows a fluorescence image taken for the device filled with the green dye at 5 minutes after the green dye solution in the channels was replaced with the red dye solution. FIG. 9A indicates that very little red dye has diffused into the reaction chambers after 5 minutes of the fluid exchange. FIG. 9B show a fluorescence image of the device at 30 minutes after the green dye solution in the channels was replaced with the red dye solution. FIG. 9C and FIG. 9D show the time-lapse profiles of fluorescence intensity long the indicated cutline for the green dye and red dye, respectively. The arrows in FIG. 9A and FIG. 9B indicate flow direction. As shown in FIG. 9C, 78.4% of the green dye was exchanged after 20 min, while the red dye diffused into the chambers even after 60 min as shown in FIG. 9D.

Figure 10A:
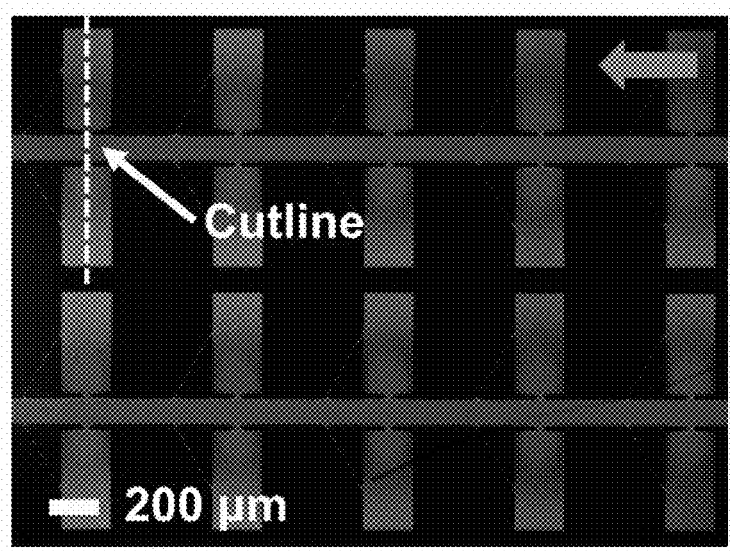
FIG. 10A-FIG. 10D show the fluorescence micrographs and diffusion profiles of a red dye in a microfluidic device with leak channel that was filled with a green dye.
Figure 10B:
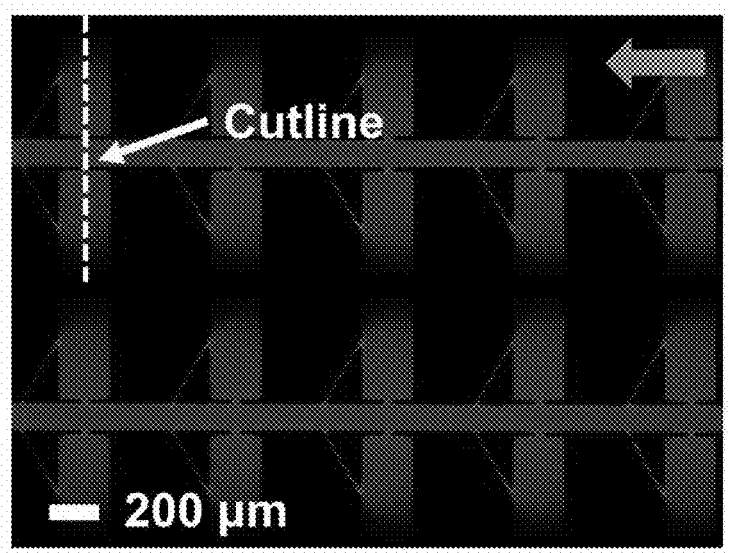
Figure 10C:
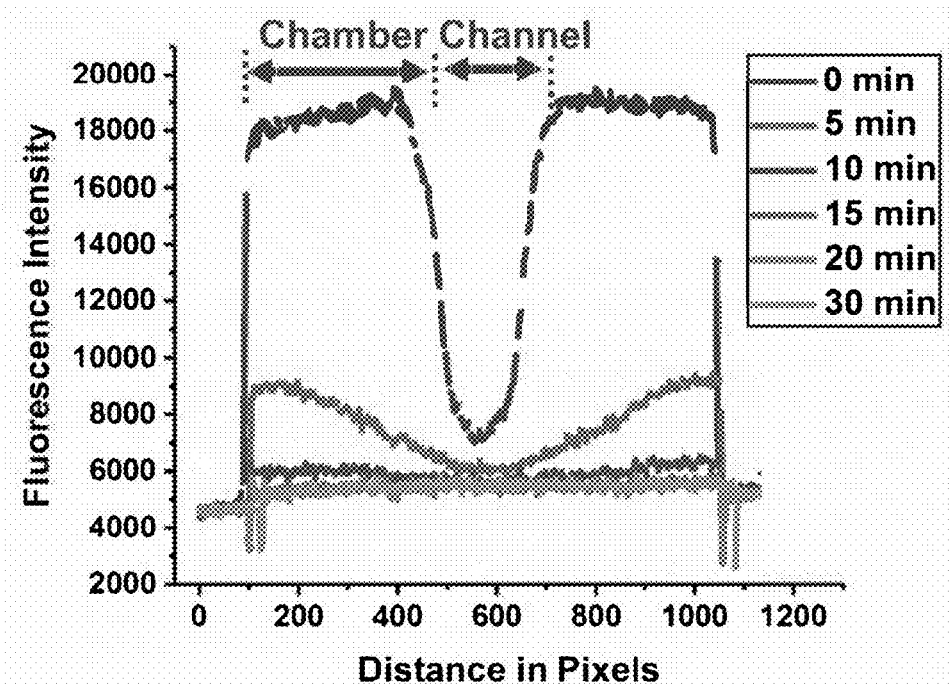
Figure 10D:
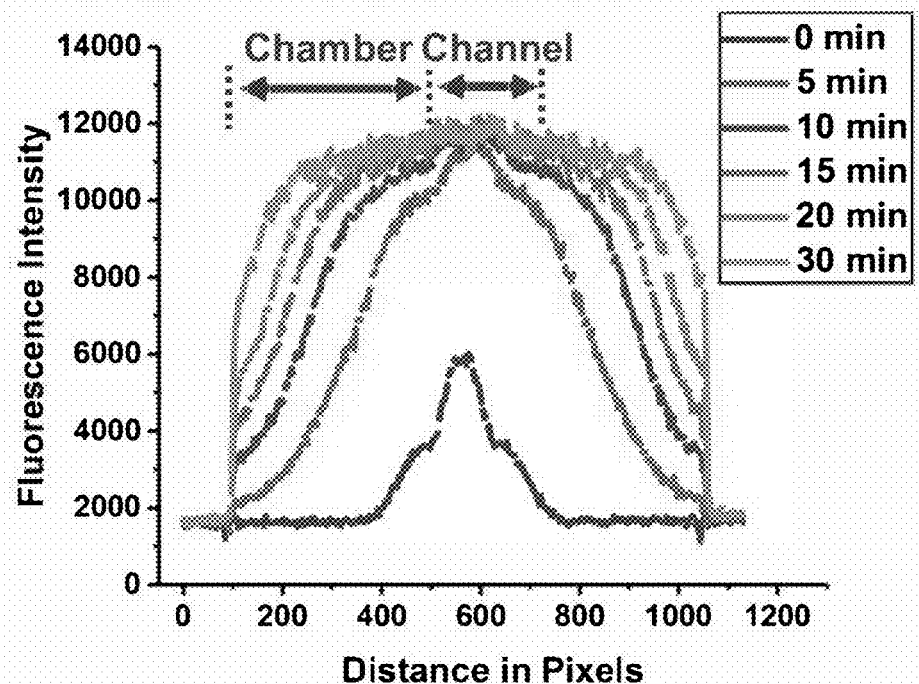

The same experiment was repeated with an exemplary microfluidic device with leak channel disclosed herein. Similarly, FIG. 10A shows a fluorescence image taken for the device filled with the green dye at 5 minutes after the green dye solution in the channels was replaced with the red dye solution. Compared to FIG. 9A, FIG. 10A clearly indicates that much more red dye has diffused into the reaction chambers after 5 minutes of the fluid exchange. FIG. 10B show a fluorescence image of the device at 30 minutes after the green dye solution in the channels was replaced with the red dye solution. FIG. 10C and FIG. 10D show the time-lapse profiles of fluorescence intensity long the indicated cutline for the green dye and red dye, respectively. The arrows in FIG. 10A and FIG. 10B indicate flow direction.

The higher efficiency of fluid exchange in the device with leak channel by both convection and diffusion contrasts to the slow rate of fluid exchange by diffusion alone in the device without leak channel. In the device with leak channels, the green dye solution could be completely replaced within 10 min and the red dye reached the end (furthest edge) of reaction chambers after only 5 min. Therefore, the leak channel design allows the DEP buffer to be replaced with a reagent solution rapidly if necessary, which in turn decreases potential alteration of a target molecule and increases ease of use.

While this invention may be embodied in many different forms, the described scientific papers and other referenced materials mentioned herein are incorporated by reference in their entirety. Furthermore, the invention encompasses any possible combination of some or all of the various embodiments mentioned herein, described herein and/or incorporated herein. In addition, the invention encompasses any possible combination that also specifically excludes any one or some of the various embodiments mentioned herein, described herein and/or incorporated herein.

The above disclosure is intended to be illustrative and not exhaustive. This description will suggest many variations and alternatives to one of ordinary skill in this art. All these alternatives and variations are intended to be included within the scope of the following claims where the term "comprising" means "including, but not limited to". Those familiar with the art may recognize other equivalents to the specific embodiments described herein which equivalents are also intended to be encompassed by the following claims.

What is claimed is:

1. A microfluidic device comprising:
one or more arrays of cell assay units; and
one or more fluidic microchannels that are configured to retain and move an ionically conductive solution,
wherein the one or more arrays of the cell assay units are placed along the one or more fluidic microchannels;
wherein each array of the cell assay units comprises two or more cell assay units;
wherein each of the cell assay units comprises a reaction chamber, micropocket, a leak channel, and at least one wireless bipolar electrode (BPE);

wherein the micropocket fluidically connects the reaction chamber and the one or more fluidic microchannels; and wherein the leak channel fluidically connects the reaction chamber and the one or more fluidic microchannels.

2. The microfluidic device of claim 1, wherein the microfluidic device comprises 8, 16, 32, 64, 128 or 256 fluidic microchannels.

3. The microfluidic device of claim 1, wherein two or more microchannels are grouped together by fluidic connection at their respective end and then connect to another group of microchannels; and/or wherein two or more microchannels are merged together into a bigger channel or reservoir.

4. The microfluidic device of claim 1, wherein the cell assay units resides inside side, bottom, top, circular wall(s), or a combination thereof of the one or more fluidic microchannels.

5. The microfluidic device of claim 1, wherein the cell assay units resides inside both side walls of the one or more fluidic microchannels.

6. The microfluidic device of claim 1, wherein the reaction chamber is fluidically connected to the micropocket and/or the leak channel at an angle of from about 15 to 90°.

7. The microfluidic device of claim 1, wherein the micropocket has an opening to the fluidic microchannel and another opening to the reaction chamber of the same cell assay unit.

8. The microfluidic device of claim 1, wherein the cell assay unit comprises a BPE in its micropocket, or wherein the cell assay unit further comprises two or more split BPEs inside the reaction chamber.

9. The microfluidic device of claim 1, wherein the bipolar electrode has one or two triangular ends, or wherein the bipolar electrode has a circular tip at one or two of its ends.

10. The fluidic device of claim 1, wherein the wall(s) of the fluidic microchannels, reaction chambers, micropockets, or leak channels comprise polydimethylsiloxane, polymethylmethacrylate (PMMA), a polymeric material, glass material, or a combination thereof.

11. A method of isolating a cell from a biological matrix for analysis comprising:
contacting a biological sample with the one or more fluidic channels of the fluidic device of claim 1, wherein the contact is to flow the biological sample through the one or more fluidic channel of the fluidic device, and
applying an AC electric field to the bipolar electrodes in the micropockets for a period of time so a targeted cell is trapped at the tip of the bipolar electrode inside the micropocket,
wherein the targeted cell is subsequently transferred to a reaction chamber for analysis or characterization; and
wherein the biological sample contains a targeted cell to be isolated.

12. The method of claim 11, wherein the method further comprises turning off the AC electric field to transfer the targeted cell from the micropocket to the reaction chamber.

13. The method of claim 12, wherein the method further comprises turning on the AC electric field after said turning off.

14. The method of claim 11, wherein the method further comprises washing the one or more fluidic microchannels with an ionically conductive solution.

15. The method of claim 11, wherein the fluidic device further comprises one or more split BPEs inside each of the reaction chambers; wherein the method further comprises lyse the targeted cell inside the reaction chamber, using an electric field between the split BPEs.

16. The method of claim 11, wherein the method further comprises washing the one or more fluidic microchannels with an ionically conductive solution when the AC electric field is on.

17. The method of claim 11, wherein the biological matrix is a blood sample and wherein the targeted cell is a circulating tumor cell (CTC).

18. The method of claim 11, wherein the sample solution has a linear flow velocity from about 0.1 µm/s to about 150 µm/s.

19. The microfluidic device of claim 1, wherein the reaction chamber of one cell assay unit is fluidically isolated from the reaction chamber of a neighboring cell assay unit.

* * * * *